United States Patent [19]
DeFeo-Jones et al.

[11] Patent Number: 6,143,864
[45] Date of Patent: *Nov. 7, 2000

[54] PEPTIDES

[75] Inventors: Deborah DeFeo-Jones, Lansdale; Dong-Mei Feng, Harleysville; Victor M. Garsky, Blue Bell; Raymond E. Jones, Lansdale; Allen I. Oliff, Gwynedd Valley, all of Pa.

[73] Assignee: Merck & Co., Inc., Rahway, N.J.

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/468,161

[22] Filed: Jun. 6, 1995

Related U.S. Application Data

[63] Continuation-in-part of application No. 08/404,833, Mar. 15, 1995, abandoned, which is a continuation-in-part of application No. 08/267,092, Jun. 28, 1994, Pat. No. 5,599,686.

[51] Int. Cl.$^7$ .............................. A61K 38/14; C07K 9/00
[52] U.S. Cl. .................... 530/322; 530/324; 530/326; 530/328; 530/329; 514/12; 514/13; 514/14; 514/15; 514/16; 514/17
[58] Field of Search ................................. 530/324, 326, 530/328, 329, 322; 514/14, 15, 13, 12, 16, 17

[56] References Cited

U.S. PATENT DOCUMENTS

| | | | |
|---|---|---|---|
| 4,277,466 | 7/1981 | Trouet | 424/185.1 |
| 4,296,105 | 10/1981 | Baurain et al. | 424/185.1 |
| 4,388,305 | 6/1983 | Trouet et al. | 424/185.1 |
| 4,446,122 | 5/1984 | Chu et al. | 435/4 |
| 4,703,107 | 10/1987 | Monsigny et al. | 530/330 |
| 4,753,984 | 6/1988 | Delmotte et al. | 530/350 |
| 4,828,831 | 5/1989 | Hannart et al. | 424/185.1 |
| 4,870,162 | 9/1989 | Trouet et al. | 530/363 |
| 5,024,835 | 6/1991 | Rao et al. | 514/8 |
| 5,030,620 | 7/1991 | Hannart et al. | 514/8 |
| 5,220,001 | 6/1993 | Ok et al. | 536/6.4 |
| 5,288,612 | 2/1994 | Griffin et al. | 435/23 |
| 5,349,066 | 9/1994 | Kaneko et al. | 536/23.1 |
| 5,391,723 | 2/1995 | Priest | 536/23.1 |
| 5,599,686 | 2/1997 | DeFeo-Jones et al. | 435/23 |
| 5,866,679 | 2/1999 | DeFeo-Jones et al. | 530/322 |

FOREIGN PATENT DOCUMENTS

| | | |
|---|---|---|
| 0 126 344 A2 | of 0000 | European Pat. Off. . |
| 0 554 708 A1 | 8/1993 | European Pat. Off. . |
| 0 590 530 A2 | 4/1994 | European Pat. Off. . |
| 2 678 274 A1 | 12/1992 | France . |
| WO 9605863A1 | of 0000 | WIPO . |
| WO 92/01936 | 2/1992 | WIPO . |
| WO 94/10343 | 5/1994 | WIPO . |
| WO 94/20114 | 9/1994 | WIPO . |
| WO 95/30758 | 11/1995 | WIPO . |

OTHER PUBLICATIONS

Proc. Natl. Acad. Sci. USA, vol. 83, pp. 3166–3170 (1986) Biochemistry, by Watt, et al.
Eur. J. Biochem., vol. 194, pp. 755–763 (1990), by Christensson, et al.
J. Med. Chem, vol. 26, pp. 633–638 (1983), by Chakravarty, et al.
J. of Med. Chem, vol. 26, No. 5, pp. 638–644 (1983), by Chakravarty, et al.
Eur. J. Biochem, vol. 95, pp. 115–119 (1979), by Pozsgay, et al.
Anal. Biochem., vol. 193, pp. 248–255 (1991), by Harnois-Pontoni, et al.
J. Med. Chem., vol. 34, pp. 3029–3035 (1991), by Mayer, et al.
Lilja, H. and Lundwall, A., "Molecular cloning of epididymal and seminal vesicular transcripts encoding a semenogelin–related protein," Proc. Natl. Acad, Sci. USA, Biochemistry, vol. 89, pp. 4559–4563 (1992).
Lilja, H., et al., "Semenogelin, the Predominant Protein in Human Semen," The Jour. of Biol. Chem., vol. 264, No. 3, pp. 1894–1900 (1989).
Trail, P.A., et al., Cure of Xenografted Human Carcinomas by BR96–Doxorubicin Immunoconjugates, Science, vol. 261, pp. 212–215 (1993).
Willner, D. et al., (6–Maleimidocaproyl)hydrazone of Doxorubicin—A New Derivative for the Preparation of Immunoconjugates of Doxorubicin, Bioconjugate Chem., vol. 4, pp. 521–527 (1993).
Yu, H., et al., Immunoreactive Prostate–Specific Antigen Levels in Female and Male Breast Tumors and its Association with Steroid Hormone Receptors and Patient Age, Clinical Biochemistry, vol. 27, pp. 75–79 (1994).
Rao, K.S.P.B., et al., Vinblastin–23–oyl Amino Acid Derivatives: Chemistry, Physiochemical Data, Toxicity, and Antitumor Activities against P388 and L1210 Leukemias, Jour. Med. Chem., vol. 28, pp. 1079–1088 (1985).
Barnett, C.J., et al., Structure–Activity Relationships of Dimeric Catharanthus Alkaloids. 1. Deacetylyinblastine Amide (Vindesine) Sulfate, Jour. Med. Chem., vol. 21, No. 1 (1978).

*Primary Examiner*—Dwayne C. Jones
*Assistant Examiner*—C. Delacroix-Muirhead
*Attorney, Agent, or Firm*—David A. Muthard; Mark R. Daniel

[57] ABSTRACT

Oligopeptides which comprise amino acid sequences that are recognized and proteolytically cleaved by free prostate specific antigen (PSA) are described. Also described are assays which comprise such oligopeptides useful for determining free PSA protease activity in vitro and in vivo. Therapeutic agents which comprise conjugates of such oligopeptides and known cytotoxic agents are also described.

8 Claims, 9 Drawing Sheets

1: MetLysProAsnIleIlePheValLeuSerLeuLeuLeuIleLeuGluLysGlnAlaAla –
21: ValMetGlyGlnLysGlyGlySerLysGlyArgLeuProSerGluPheSerGlnPhePro –
41: HisGlyGlnLysGlyGlnHisTyrSerGlyGlnLysGlyLysGlnGlnThrGluSerLys –
61: GlySerPheSerIleGlnTyrThrTyrHisValAspAlaAsnAspHisAspGlnSerArg –
81: LysSerGlnGlnTyrAspLeuAsnAlaLeuHisLysThrThrLysSerGlnArgHisLeu –
101: GlyGlySerGlnGlnLeuLeuHisAsnLysGlnGluGlyArgAspHisAspLysSerLys –
121: GlyHisPheHisArgValValIleHisHisLysGlyGlyLysAlaHisArgGlyThrGln –
141: AsnProSerGlnAspGlnGlyAsnSerProSerGlyLysGlyIleSerSerGlnTyr|Ser –
   (CS#5)
161: AsnThrGluGluArgLeuTrpValHisGlyLeuSerLysGluGlnThrSerValSerGly –
181: AlaGlnLysGlyArgLysGlnGlyGlySerGlnSerSerTyrValLeuGlnThrGluGlu –
201: LeuValAlaAsnLysGlnGlnArgGluThrLysAsnSerHisGlnAsnLysGlyHisTyr –
221: GlnAsnValValGluValArgGluGluHisSerSerLysValGlnThrSerLeuCysPro –
241: AlaHisGlnAspLysLeuGlnHisGlySerLysAspIlePheSerThrGlnAspGluLeu –

FIG.1a

261: LeuValTyrAsnLysAsnGlnHisGlnThrLysAsnLeuAsnGlnAspGlnGlnHisGly –
        CS#3
281: ArgLysAlaAsnLysIleSerTyrGln|SerSerSerThrGluGluArgArgLeuHisTyr –
        CS#4
301: GlyGluAsnGlyValGlnLysAspValSerGlnSerSerIleTyrSer|GlnThrGluGlu –

321: LysAlaGlnGlyLysSerGlnLysGlnIleThrIleProSerGlnGluGlnGluHisSer –
        CS#1
341: GlnLysAlaAsnLysIleSerTyrGln|SerSerSerThrGluGluArgArgLeuHisTyr –
        CS#2
361: GlyGluAsnGlyValGlnLysAspValSerGlnArgSerIleTyrSer|GlnThrGluLys –

381: LeuValAlaGlyLysSerGlnIleGlnAlaProAsnProLysGlnGluProTrpHisGly –

401: GluAsnAlaLysGlyGluSerGlyGlnSerThrAsnArgGluGlnAspLeuLeuSerHis –

421: GluGlnLysGlyArgHisGlnHisGlySerHisGlyGlyLeuAspIleValIleIleGlu –

441: GlnGluAspAspSerAspArgHisLeuAlaGlnHisLeuAsnAsnAspArgAsnProLeu –

461: PheThr –

FIG.1b

PERCENT PEPTIDE HYDROLYSIS

TIME OF INCUBATION (HOURS)

| PEPTIDE | 0.5 | 1 | 2 | 3 | 4 | 20 |
|---|---|---|---|---|---|---|
| 1. SYQSSSTE | ND | 0 | ND | 0 | ND | 0 |
| 2. ISYQSSSTE | ND | 0 | ND | 0 | ND | 0 |
| 3. KISYQSSSTE | ND | 10 | ND | 30 | ND | 90 |
| 4. NKISYQSSSTE | ND | 30 | ND | 70 | ND | 100 |
| 5. NKISYQSSST | ND | 20 | 30 | ND | ND | 100 |
| 6. ANKISYQSSSTE | 15 | 25 | ND | ND | 80 | 100 |
| 7. ANKISYQSSS | 4 | 6 | 16 | 30 | 45 | ND |
| 8. NKISYQSSS | 2 | 6 | 22 | 44 | 55 | ND |
| 9. ANKISYQSS | 1 | ND | 12 | ND | 39 | ND |
| 10 GRKANKISYQS-SSTEERRLHYGEN G | 20 | 50 | ND | ND | 90 | 100 |

FIG.2

| PEPTIDE | SEQ. ID. NO. | % PEPTIDE CLEAVED AT 4 HOURS BY YORK PSA |
|---|---|---|
| SEMENOGELIN (463 aa) |  | 100 (30 min) |
| GRKANKISYQ-SSSTEERRLHYGENG | 6 | 100 (2 hrs) |
| SQKANKISYQ-SSSTEERRLHYGENG | 67 | 100 (3 hrs) |
| ANKISYQ-SSSTE | 11 | 98 |
| ISYQ-SSST | 68 | 0 |
| NKISYQ-SSST | 10 | 62 |
| NKISYQ-SSSTE | 3 | 90 |
| KISYQ-SSSTE | 9 | 49 |
| SYQ-SSSTE | 7 | 0 (3 hrs) |
| ISYQ-SSSTE | 8 | 0 |
| NKISYQ-SSS | 17 | 55 |
| ANKISYQ-SSS | 18 | 45 |
| ANKISYQ-SS | 69 | 39 |
|  |  |  |
| ANKISYQ-SSSTE-amide | 11 | 43 |
| Ac-ANKISYQ-SSSTL | 70 | 57 |
|  |  |  |
| Ac-ANKISYQ-SSSTE-amide | 11 | 40 |
| Ac-ANKISYQ-SSSTL-amide | 70 | 46 |
| Ac-ANGISYQ-SSSTE-amide | 71 | 0 |
| Ac-ANPISYQ-SSSTE-amide | 72 | 0 |
| Ac-ANKISYQ-SASTE-amide | 73 | 66 |
| Ac-ANKISYQ-SSKTE-amide | 74 | 80 |
| Ac-ANKISYQ-SSTE-amide | 75 | 44 |
| Ac-ANKI(dS)YQ-SSSTE-amide | 76 | 9 |
| Ac-ANK(dI)SYQ-SSSTE-amide | 77 | 0 |
| Ac-ANKISYQ-SSQTE-amide | 78 | 55 |
| Ac-ANKISYQ-SAKTE-amide | 79 | 80 |
| Ac-AN(dK)ISYQ-SSSTE-amide | 80 | 3 |
| Ac-ANKISYQ-STE-amide | 81 | 28 |
| Ac-ANKIYQ-SSTE-amide | 82 | 0 |
| Ac-ANKSYQ-SSTE-amide | 83 | 10 |
| Ac-ANKASYQ-SASTE-amide | 84 | 98 |
| Ac-ANEISYQ-SASTE-amide | 85 | 10 |
| Ac-NKISYQ-SS-amide | 16 | 30 |
| Ac-KISYQ-SS-amide | 86 | 15 |
| Ac-SYQ-SSTE-amide | 87 | 65 |
| Ac-SYQ-SSTL-acid | 88 | 83 |
| Ac-ASYQ-SSTE-amide | 89 | 68 |
| Ac-EISYQ-SSSTE-amide | 90 | 0 |
| Ac-ANEISYQ-SSSTE-amide | 91 | 0 |
| Ac-ANKISYY-SSSTE-amide | 92 | 73 |
| Ac-ANKISYY-SASTE-amide | 93 | 91 |

FIG. 3a

| PEPTIDE | L-NUMBER | % PEPTIDE CLEAVED AT 4 HOURS BY YORK PSA |
|---|---|---|
| Ac-ASYQ-SSL-acid | 94 | 71 |
| Ac-ANSYQ-SSSTE-amide | 95 | 28 |
| Ac-ASYQ-SSSTE-amide | 96 | 64 |
| Ac-SYQ-SSSTE-amide | 97 | 50 |
| Ac-ANKASYQ-SASC-amide | 98 | 78 |
| Ac-Q-SSTE-amide | 99 | 0 |
| Ac-YQ-SSTE-amide | 100 | 0 |
| Ac-SQ-SSTE-amide | 101 | 0 |
| Ac-ANKISQ-SSTE-amide | 102 | 0 |
| AC-AN(ORN)ISYQ-SSTE-amide | 103 | 34 |
| Ac-S(3PAL)Q-SSTE-amide | 104 | 4 |
| Ac-S(3,4-C12F)Q-SSTE-amide | 105 | 6 |
| Ac-SKQ-SSTE-amide | 106 | 0 |
| Ac-SYQ-SSTL-acid | 88 | 81 |
| Ac-SYQ-SSSL-acid | 107 | 98 |
| (e-ACA)-YQ-SSSL-amide | 108 | 0 |
| ANK(N-Me-I)SYQ-SSTE-amide | 109 | 0 |
| SYQ-SSTE-amide | 110 | 0 |
| HO(CH2)2CO-YQ-SSTE-amide | 111 | 0 |
| Ac-SYK-SSTE-amide | 112 | 5 |
| Ac-SYY-SSTE-amide | 113 | 93 |
| Ac-SYQ-SSL-NHNH2 | 114 | 32 |
| Ac-SYQ-SSL-acid | 115 | 72 |
| DAP-YQ-SSSL-amide | 116 | 0 |

FIG.3b

| DOXORUBICIN-CONGENER | SEQ.ID.NO | % PEPTIDE CLEAVED AT 4 HOURS BY YORK PSA |
|---|---|---|
| Ac-ANKISYQ-SSST-DOX (3') | 117 | 20(1 hr) NO SAMPLE LEFT |
| Ac-ANKISYQ-SSSTL-DOX (3') | 70 | 87 |
| Ac-ANKASYQ-SASTL-DOX (3') | 118 | NA |
| Ac-ANKASYQ-SASL-DOX (3') | 119 | 100 (3 hr) |
| Ac-ANKASYQ-SSSL-DOX (3') | 120 | 100 (3 hrs) |
| Ac-ANKASYQ-SSL-DOX (3') | 121 | 91 |
| Ac-SYQ-SST(dL)-DOX (3') | 122 | 17 |
| Ac-SYQ-SSSL-DOX (3') | 107 | 95 (PARTIALLY SOLUBLE) |
| Ac-ANKASYA-SSSL-DOX (3') | 123 | 0 |
| Ac-KYQ-SSSL-DOX (3') | 124 | 98 (PARTIALLY SOLUBLE) |
| Ac-SYQ-SSKL-DOX (3') | 125 | 88 |
| Ac-SYQ-SSK(dL)-DOX (3') | 126 | 87 |

FIG.5

| DOXORUBICIN-CONGENER | SEQ. ID. NO | % PEPTIDE CLEAVED/ LNCaP MEDIA 4 HR | % PEPTIDE CLEAVED/ DuPRO MEDIA 4 HR |
|---|---|---|---|
| Ac-ANKASYQ-SASL-DOX (3') | 119 | 92 | 13 |
| Ac-ANKASYQ-SSSL-DOX (3') | 121 | 98 | 13 |
| Ac-ANKASYQ-SSSL-DOX (3') | 122 | 95 | 27 |
| Ac-SYQ-SSSL-DOX (3') | 107 | 63 | 0 |

FIG.6

| DOXORUBICIN-CONGENER | SEQ. ID. NO | LNCaP CELL KILL EC50 (μM) |
|---|---|---|
| Ac-ANKISYQ-SSST-DOX (3') | 117 | > 100 |
| Ac-ANKISYQ-SSSTL-DOX (3') | 70 | 8.4 |
| Ac-ANKASYQ-SASTL-DOX (3') | 118 | 31 |
| Ac-ANKASYQ-SASL-DOX (3') | 119 | 16 (DuPRO > 100) |
| Ac-ANKASYQ-SSSL-DOX (3') | 120 | 15 |
| Ac-ANKASYQ-SSL-DOX (3') | 121 | 6.5 (DuPRO = 117) |
| Ac-SYQ-SSSL-DOX (3') | 107 | 20(DuPRO>100) (PARTIALLY SOLUBLE) |
| Ac-ANKASYA-SSSL-DOX (3') | 123 | > 100 |
| Ac-KYQ-SSSL-DOX (3') | 124 | 6.5 (DuPRO > 100) |
| Ac-SYQ-SSKL-DOX (3') | 125 | 11.8 (DuPRO > 100) |
| Ac-SYQ-SSK(dL)-DOX (3') | 126 | >100 (DuPRO > 100) |
| Ac-hRYQ-SSSL-DOX (3') | 145 | 6.4 (DuPRO > 100) |
| Ac-KYQ-SSS(Nle)-DOX (3') | 146 | 4.4 (DuPRO > 100) |

FIG.7

PEPTIDES

RELATED APPLICATION

The present patent application is a Continuation-in-Part application of application Ser. No. 08/404,833, filed Mar. 15, 1995, now abandoned, which itself is a Continuation-in-Part application of application Ser. No. 08/267,092, filed Jun. 28, 1994, now U.S. Pat. No. 5,599,686.

BACKGROUND OF THE INVENTION

In 1994 cancer of the prostate gland is expected to be diagnosed in 200,000 men in the U.S. and 38,000 American males will die from this disease (Garnick, M. B. (1994). The Dilemmas of Prostate Cancer. Scientific American, April:72–81). Thus, prostate cancer is the most frequently diagnosed malignancy (other than that of the skin) in U.S. men and the second leading cause of cancer-related deaths (behind lung cancer) in that group.

Prostate specific Antigen (PSA) is a single chain 33 kDa glycoprotein that is produced almost exclusively by the human prostate epithelium and occurs at levels of 0.5 to 2.0 mg/ml in human seminal fluid (Nadji, M., Taber, S. Z., Castro, A., et al. (1981) Cancer 48:1229; Papsidero, L., Kuriyama, M., Wang, M., et al. (1981). JNCI 66:37; Qui, S. D., Young, C. Y. F., Bihartz, D. L., et al. (1990), J. Urol. 144:1550; Wang, M. C., Valenzuela, L. A., Murphy, G. P., et al. (1979). Invest. Urol. 17:159). The single carbohydrate unit is attached at asparagine residue number 45 and accounts for 2 to 3 kDa of the total molecular mass. PSA is a protease with chymotrypsin-like specificity (Christensson, A., Laurell, C. B., Lilja, H. (1990). Eur. J. Biochem. 194:755–763). It has been shown that PSA is mainly responsible for dissolution of the gel structure formed at ejaculation by proteolysis of the major proteins in the sperm entrapping gel, Semenogelin I and Semenogelin II, and fibronectin (Lilja, H. (1985). J. Clin. Invest. 76:1899; Lilja, H., Oldbring, J., Rannevik, G., et al. (1987). J. Clin. Invest. 80:281; McGee, R. S., Herr, J. C. (1988). Biol. Reprod. 39:499). The PSA mediated proteolysis of the gel-forming proteins generates several soluble Semenogelin I and Semenogelin II fragments and soluble fibronectin fragments with liquefaction of the ejaculate and release of progressively motile spermatoza (Lilja, H., Laurell, C. B. (1984). Scand. J. Clin. Lab. Invest. 44:447; McGee, R. S., Herr, J. C. (1987). Biol. Reprod. 37:431). Furthermore, PSA may proteolytically degrade IGFBP-3 (insulin-like growth factor binding protein 3) allowing IGF to stimulate specifically the growth of PSA secreting cells (Cohen et al., (1992) J. Clin. Endo. & Meta. 75:1046–1053).

PSA complexed to alpha 1-antichymotrypsin is the predominant molecular form of serum PSA and may account for up to 95% of the detected serum PSA (Christensson, A., Björk, T., Nilsson, O., et al. (1993). J. Urol. 150:100–105; Lilja, H., Christensson, A., Dahlén, U. (1991). Clin. Chem. 37:1618–1625; Stenman, U. H., Leinoven, J., Alfthan, H., et al. (1991). Cancer Res. 51:222–226). The prostatic tissue (normal, benign hyperplastic, or malignant tissue) is implicated to predominantly release the mature, enzymatically active form of PSA, as this form is required for complex formation with alpha 1-antichymotrypsin (Mast, A. E., Enghild, J. J., Pizzo, S. V., et al. (1991). Biochemistry 30:1723–1730; Perlmutter, D. H., Glover, G. I., Rivetna, M., et al. (1990). Proc. Natl. Acad. Sci. USA 87:3753–3757). Therefore, in the microenvironment of prostatic PSA secreting cells the PSA is believed to be processed and secreted in its mature enzymatically active form not complexed to any inhibitory molecule. PSA also forms stable complexes with alpha 2-macroglobulin, but as this results in encapsulation of PSA and complete loss of the PSA epitopes, the in vivo significance of this complex formation is unclear. A free, noncomplexed form of PSA constitutes a minor fraction of the serum PSA (Christensson, A., Björk, T., Nilsson, O., et al. (1993). J. Urol. 150:100–105; Lilja, H., Christensson, A., Dahlén, U. (1991). Clin. Chem. 37:1618–1625). The size of this form of serum PSA is similar to that of PSA in seminal fluid (Lilja, H., Christensson, A., Dahlén, U. (1991). Clin. Chem. 37:1618–1625) but it is yet unknown as to whether the free form of serum PSA may be a zymogen; an internally cleaved, inactive form of mature PSA; or PSA manifesting enzyme activity. However, it seems unlikely that the free form of serum PSA manifests enzyme activity, since there is considerable (100 to 1000 fold) molar excess of both unreacted alpha 1-antichymotrypsin and alpha 2-macroglobulin in serum as compared with the detected serum levels of the free 33 kDa form of PSA (Christensson, A., Björk, T., Nilsson, O., et al. (1993). J. Urol. 150:100–105; Lilja, H., Christensson, A., Dahlén, U. (1991). Clin. Chem. 37:1618–1625).

Serum measurements of PSA are useful for monitoring the treatment of adenocarcinoma of the prostate (Duffy, M. S. (1989). Ann. Clin. Biochem. 26:379–387; Brawer, M. K. and Lange, P. H. (1989). Urol. Suppl. 5:11–16; Hara, M. and Kimura, H. (1989). J. Lab. Clin. Med. 113:541–548), although above normal serum concentrations of PSA have also been reported in benign prostatic hyperplasia and subsequent to surgical trauma of the prostate (Lilja, H., Christensson, A., Dahlén, U. (1991). Clin. Chem. 37:1618–1625). Prostate metastases are also known to secrete immunologically reactive PSA since serum PSA is detectable at high levels in prostatectomized patients showing widespread metatstatic prostate cancer (Ford, T. F., Butcher, D. N., Masters, R. W., et al. (1985). Brit. J. Urology 57:50–55). Therefore, a cytotoxic compound that could be activated by the proteolytic activity of PSA should be prostate cell specific as well as specific for PSA secreting prostate metastases.

Accordingly, it is the object of this invention to provide novel oligopeptides which selectively are enzymatically cleaved by active free prostate specific antigen (PSA).

It is also the object of this invention to provide a quantitative assay for enzymatically active PSA which incorporates those novel oligopeptides.

It is further the object of this invention to provide a novel anti-cancer composition useful for the treatment of prostate cancer which comprises those novel oligopeptides in conjugation with a cytotoxic agent.

Another object of this invention is to provide a method of treating prostate cancer which comprises administration of novel anti-cancer composition.

SUMMARY OF THE INVENTION

The several points of cleavage where semenogelin I is selectively proteolytically cleaved by free PSA have been identified. Oligopeptides which comprise the amino acid sequences that are recognized and proteolytically cleaved by free prostate specific antigen (PSA) are described. Such oligopeptides are useful in assays-which can determine the free PSA protease activity in vitro and in vivo. Furthermore, such oligopeptides may be incorporated into therapeutic agents which comprise conjugates of such oligopeptides and known cytotoxic agents and which are useful in the treatment of prostatic cancer.

BRIEF DESCRIPTION OF THE FIGURES

FIGS. 1a and 1b: Primary Amino Acid Sequence of Semenogelin I: The primary amino acid sequence of Semenogelin I is shown. (SEQ.ID.NO.: 1) The PSA proteolytic cleavage sites ("CS") are shown (numbered in order of the relative affinity of a site towards PSA hydrolysis) and the protein fragments are numbered sequentially starting at the amino terminus.

FIG. 2: Cleavage Affinity of Synthetic Oligopeptides: A nested set of synthetic oligopeptides was prepared and the oligopeptides were digested with enzymaticaaly active free PSA for various times. The results are shown. The following SEQ. ID. NOs. apply to the peptides listed in the Figure: peptide 1 - SEQ. ID. NO. 7; peptide 2 - SEQ. ID. NO. 8; peptide 3 - SEQ. ID. NO. 9; peptide 4 - SEQ. ID. NO. 3; peptide 5 - SEQ. ID. NO. 10; peptide 6 - SEQ. ID. NO. 11; peptide 7 - SEQ. ID. NO. 18; peptide 8 - SEQ. ID. NO. 17; peptide 9 - SEQ. ID. NO. 69; and peptide 10 - SEQ. ID. NO. 6;

FIGS. 3a and 3b: Cleavage Affinity of Synthetic Oligopeptides: Synthetic oligopeptides were prepared and the oligopeptides were digested with enzymatically active free PSA for four (4) hours. The percentage of the oligopeptide that is cleaved in this period of time is listed. The results are shown in FIG. 4.

FIG. 5: Cleavage Affinity of Oligopeptides in Conjugation with Doxorubicin by Free PSA In Vitro: Oligopeptides-doxorubicin conjugates were prepared and the conjugates were digested with enzymatically active free PSA for four (4) hours. The percentage conjugate that is enzymatically cleaved in the oligopeptide in this period of time is listed. The results are shown in the Figure.

FIG. 6: Cleavage Affinity of Oligopeptides in Conjugation with Doxorubicin in Cell Conditioned Media: Oligopeptides-doxorubicin conjugates were reacted for four (4) hours with cell culture media that had been conditioned by exposure to LNCaP cells (which are known to secrete free PSA) or DuPRO cell (which do not secrete free PSA). The percentage conjugate that is enzymatically cleaved in the oligopeptide in this period of time is listed. The results are shown in the Figure.

FIG. 7: Cytotoxicity Data of Cleavable Oligopeptide-Doxorubicin Conjugates:

Figure 4:
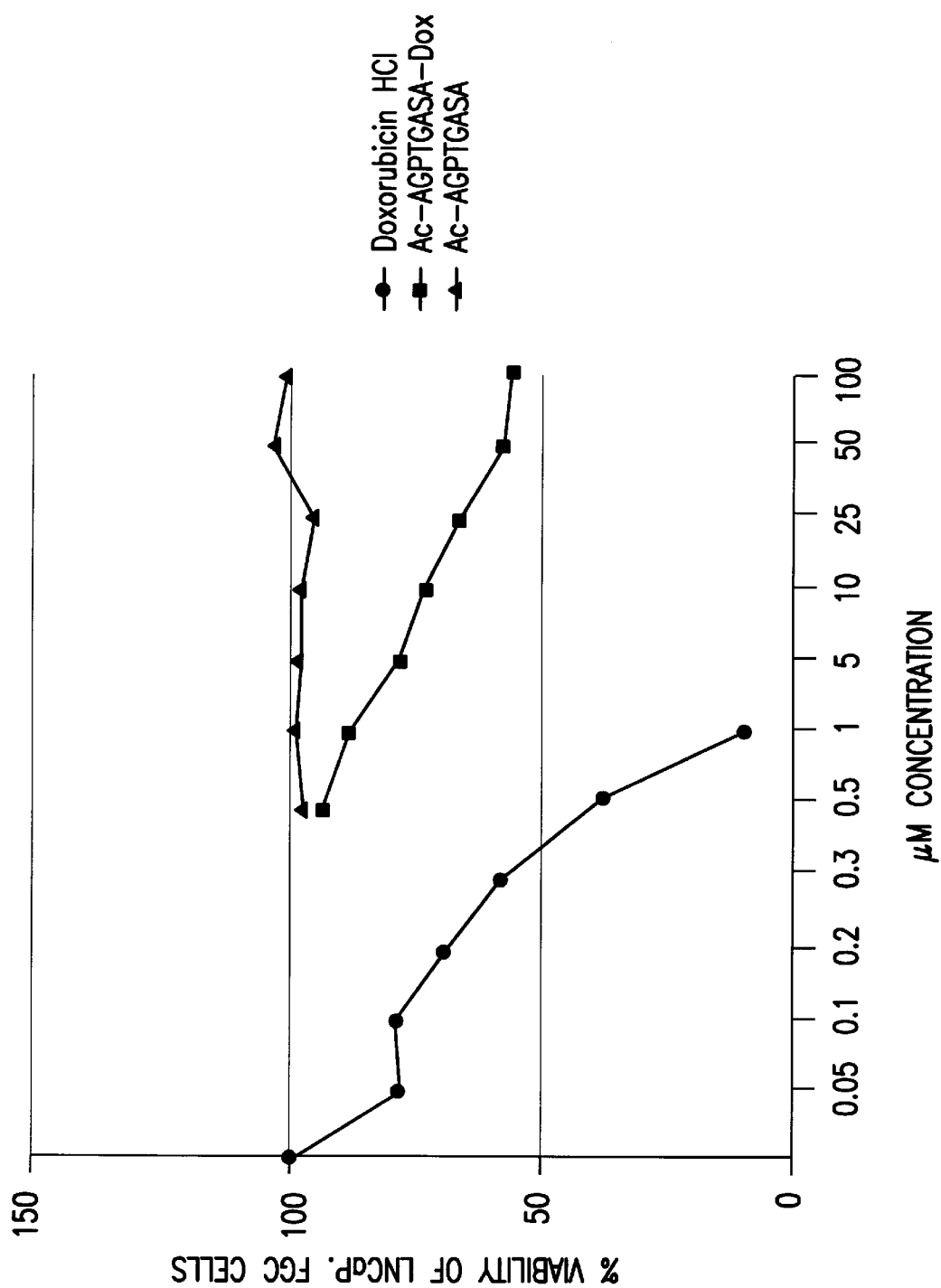
FIG. 4: Cytotoxicity Data of Non-cleavable Oligopeptide-Doxorubicin Conjugates: The data of the figure shows comparative cytotoxicity of doxorubicin and a conjugate of doxorubicin covalently bound to an oligopeptide (Compound 12d) that does not contain the free PSA proteolytic cleavage site. The $EC_{50}$ for doxorubicin is 0.3 μM, while the acetylated oligopeptide modified doxorubicin has an $EC_{50}$ that has been reduced by greater than 300 fold. This conjugate had no HPLC detectable contamination with unmodified doxorubicin. The oligopeptide alone had no detectable cell killing activity.

The data in the Figure shows cytotoxicity (as $EC_{50}$) of conjugates of doxorubicin covalently bound to an oligopeptide that contain a free PSA proteolytic cleavage site against a cancer cell line that is known to secrete free PSA. Also shown for selected conjugates is the cytotoxicity of the conjugate against a cell line (DuPRO) which does not secrete free PSA.

DETAILED DESCRIPTION OF THE INVENTION

The present invention relates to novel oligopeptides which are specifically recognized by the free prostate specific antigen (PSA) and are capable of being proteolytically cleaved by the enzymatic activity of the free prostate specific antigen. Such oligopeptides include oligomers that comprise an amino acid sequence selected from:

a) AsnLysIleSerTyrGln|Ser, (SEQ.ID.NO.: 13)

b) LysIleSerTyrGln|Ser, (SEQ.ID.NO.: 14)

c) GlyGluAsnGlyValGlnLysAspValSerGlnXaa
  SerIleTyr|SerGlnThrGlu, (SEQ.ID.NO.: 15)

d) GlyLysGlyIleSerSerGlnTyr|SerAsnThrGluGlu
  ArgLeu, (SEQ.ID.NO.: 2)

e) AsnLysIleSerTyrTyr|Ser, (SEQ.ID.NO.: 127)

f) AsnLysAlaSerTyrGln|Ser, (SEQ.ID.NO.: 128)

g) SerTyrGln|SerSer; (SEQ.ID.NO.: 129)

h) LysTyrGln|SerSer; and (SEQ.ID.NO.: 140)

i) hArgTyrGln|SerSer; (SEQ.ID.NO.: 141)

wherein hArg is homoarginine and Xaa is any natural amino acid.

In an embodiment of the instant invention, the oligopeptides include oligomers that comprise an amino acid sequence that is selected from:

a) AsnLysIleSerTyrGln|SerSer, (SEQ.ID.NO.: 16)

b) AsnLysIleSerTyrGln|SerAla, (SEQ.ID.NO.: 130)

c) AsnLysIleSerTyrGln|SerSer, (SEQ.ID.NO.: 17)

d) AlaAsnLysIleSerTyrGln|SerSerSer, (SEQ.ID.NO.: 18)

e) LysIleSerTyrGln|SerSerSerThrGlu, (SEQ.ID.NO.: 19)

f) GlyGluAsnGlyValGlnLysAspValSerGln
  ArgSerIleTyr|SerGlnThrGlu, (SEQ.ID.NO.: 4)

g) GlyGluAsnGlyValGlnLysAspValSerGlnSer
  SerIleTyr|SerGlnThrGlu, (SEQ.ID.NO.: 5)

h) AlaAsnLysIleSerTyrTyr|Ser, (SEQ.ID.NO.: 131)

i) AlaAsnLysAlaSerTyrGln|Ser, (SEQ.ID.NO.: 132)

j) SerTyrGln|SerSerThr, (SEQ.ID.NO.: 133)

k) SerTyrGln|SerSerSer, (SEQ.ID.NO.: 134)

l) LysTyrGln|SerSerSer, (SEQ.ID.NO.: 142)

m) hArgTyrGln|SerSerSer, and (SEQ.ID.NO.: 143)

n) SerTyrGln|SerSerLeu. (SEQ.ID.NO.: 135)

In a more preferred embodiment of the instant invention, the oligopeptides include oligomers that comprise an amino acid sequence that is selected from:

a) AsnLysIleSerTyrGln |SerSerSerThr, (SEQ.ID.NO.:10)

b) AlaAsnLysIleSerTyrGln|SerAla, (SEQ.ID.NO.: 136)

c) AsnLysIleSerTyrGln|SerSerSerThrGlu, (SEQ.ID.NO.:3)

d) AlaAsnLysIleSerTyrGln|SerSerSerThrGlu, (SEQ.ID.NO.: 11)

e) GlyGluAsnGlyValGlnLysAspValSerGlnArg
  SerIleTyr|SerGlnThrGlu, (SEQ.ID.NO.: 4)

f) AlaAsnLysIleSerTyrTyr|SerSer, (SEQ.ID.NO.: 137)

g) AlaAsnLysIleSerTyrTyr|SerAla, (SEQ.ID.NO.: 138)

h) AlaAsnLysAlaSerTyrGln|SerAla,          (SEQ.ID.NO.: 139)

i) AlaSerTyrGln|SerSerLeu.                (SEQ.ID.NO.: 94)

In a further embodiment of the instant invention, the oligopeptides include oligomers that comprise an amino acid sequence that is selected from:

a) GlyArgLysAlaAsnLysIleSerTyrGln|SerSerSerThrGluGluArgArg
       LeuHisTyrGlyGluAsnGly.          (SEQ.ID.NO.: 6)

The phrase "oligomers that comprise an amino acid sequence" as used hereinabove, and elsewhere in the Detailed Description of the Invention, describes oligomers of from about 6 to about 100 amino acids residues which include in their amino acid sequence the specific amino acid sequence decribed and which are therefore proteolytically cleaved within the amino acid sequence described by free PSA. Thus, for example, the following oligomer:

GlnLeuAspAsnLysIleSerTyrGln|SerSerSerThr
       HisGlnSerSer                    (SEQ.ID.NO.: 20)

comprises the amino acid sequence:

AsnLysIleSerTyrGln|SerSerSerThr       (SEQ.ID.NO.:10)

and would therefore come within the instant invention. It is understood that such oligomers do not include semenogelin I and semenogelin II.

It is also understood that the instant invention includes oligomers wherein the N-terminus amino acid or the C-terminus amino acid, or both terminus amino acids are modified. Such modifications include, but are not limited to, acylation of the amine group at the N-terminus and formation of an amide to replace the carboxylic acid at the C-terminus. Addition of such moieties may be performed during solid-phase synthesis of the oligomer; thus, attachment of the C-terminus amino acid to a solid phase resin may be through an amine which results in an amide moiety upon acidic cleavage of the oligomer from the resin. Thus the following compounds are considered "oligomers that comprise an amino acid sequence" as used hereinabove and are meant to be illustrative and are not limiting:

| Sequence | SEQ ID |
|---|---|
| AlaAsnLysIleSerTyrGln\|SerSerSerThrGlu-amide | (SEQ.ID.NO.: 11) |
| Ac-AlaAsnLysIleSerTyrGln\|SerSerSerThrLeu | (SEQ.ID.NO.: 70) |
| Ac-AlaAsnLysIleSerTyrGln\|SerSerSerThr Glu-amide | (SEQ.ID.NO.: 11) |
| Ac-AlaAsnLysIleSerTyrGln\|SerSerSerThr Leu-amide | (SEQ.ID.NO.: 70) |
| Ac-AlaAsnLysIleSerTyrGln\|SerAlaSerThr Glu-amide | (SEQ.ID.NO.: 73) |
| Ac-AlaAsnLysIleSerTyrGln\|SerSerLysThr Glu-amide | (SEQ.ID.NO.: 74) |
| Ac-AlaAsnLysIleSerTyrGln\|SerSerThr Glu-amide | (SEQ.ID.NO.: 75) |
| Ac-AlaAsnLysIleSerTyrGln\|SerSerGlnThr Glu-amide | (SEQ.ID.NO.: 78) |
| Ac-AlaAsnLysIleSerTyrGln\|SerAlaLysThr Glu-amide | (SEQ.ID.NO.:79) |
| Ac-AlaAsnLysIleSerTyrGln\|SerThrGlu-amide | (SEQ.ID.NO.: 81) |
| Ac-AlaAsnLysSerTyrGln\|SerSerThrGlu-amide | (SEQ.ID.NO.: 82) |
| Ac-AlaAsnLysAlaSerTyrGln\|SerAlaSerThr Glu-amide | (SEQ.ID.NO.: 84) |
| Ac-AlaAsnGluIleSerTyrGln\|SerAlaSerThr Glu-amide | (SEQ.ID.NO.: 85) |
| Ac-AsnLysIleSerTyrGln\|SerSer-amide | (SEQ.ID.NO.: 16) |
| Ac-LysIleSerTyrGln\|SerSer-amide | (SEQ.ID.NO.: 86) |
| Ac-SerTyrGlnSerSerThrGlu-amide | (SEQ.ID.NO.: 87) |
| Ac-AlaSerTyrGln\|SerSerThrGlu-amide | (SEQ.ID.NO.: 89) |
| Ac-AlaAsnLysIleSerTyrTyr\|SerSerSer ThrGlu-amide | (SEQ.ID.NO.: 92) |
| Ac-AlaAsnLysIleSerTyrTyr\|SerAlaSer ThrGlu-amide | (SEQ.ID.NO.: 93) |
| Ac-AlaSerTyrGln\|SerSerLeu-amide | (SEQ.ID.NO.: 94) |
| Ac-AlaAsnSerTyrGln\|SerSerSerThrGlu-amide | (SEQ.ID.NO.: 95) |
| Ac-AlaSerTyrGln\|SerSerSerThrGlu-amide | (SEQ.ID.NO.: 96) |
| Ac-SerTyrGln\|SerSerSerThrGlu-amide | (SEQ.ID.NO.: 97) |
| Ac-AlaAsnLysAlaSerTyrGln\|SerAlaSer Cys-amide | (SEQ.ID.NO.: 98) |

A person of ordinary skill in the peptide chemistry art would readily appreciate that certain amino acids in a biologically active oligopeptide may be replaced by other homologous, isosteric and/or isoelectronic amino acids wherein the biological activity of the original oligopeptide has been conserved in the modified oligopeptide. The following list of amino acid replacements is meant to be illustrative and is not limiting:

| Original Amino Acid | Replacement Amino Acid(s) |
|---|---|
| Ala | Gly |
| Arg | Lys, Ornithine |
| Asn | Gln |
| Asp | Glu |
| Glu | Asp |
| Gln | Asn |
| Gly | Ala |
| Ile | Val, Leu, Met, Nle |
| Leu | Ile, Val, Met, Nle |
| Lys | Arg, Ornithine |
| Met | Leu, Ile, Nle, Val |
| Ornithine | Lys, Arg |
| Phe | Tyr, Ttp |
| Ser | Thr |
| Thr | Ser |
| Trp | Phe, Tyr |
| Tyr | Phe,Trp |
| Val | Leu, Ile, Met, Nle |

Thus, for example, the following oligopeptides may be synthesized by techniques well known to persons of ordinary skill in the art and would be expected to be proteolytically cleaved by free PSA:

| Sequence | SEQ ID |
|---|---|
| AsnArgIleSerTyrGln\|Ser | (SEQ.ID.NO.: 21) |
| AsnLysValSerTyrGln\|Ser | (SEQ.ID.NO.: 22) |
| AsnLysMetSerTyrGln\|SerSer | (SEQ.ID.NO.: 23) |
| AsnLysLeuSerTyrGln\|SerSer | (SEQ.ID.NO.: 24) |
| AsnLysIleThrTyrGln\|SerSerSer | (SEQ.ID.NO.: 25) |
| AsnLysIleSerPheGln\|SerSerSer | (SEQ.ID.NO.: 26) |
| AsnLysIleSerTrpGln\|SerSerSerThr | (SEQ.ID.NO.: 27) |
| AsnLysIleSerTyrAsn\|SerSerSerThr | (SEQ.ID.NO.: 28) |
| AsnLysIleSerTyrGln\|ThrSerSerThr | (SEQ.ID.NO.: 29) |
| AsnLysIleSerTyrGln\|Ser | (SEQ.ID.NO.: 30) |
| GlnLysIleSerTyrGln\|SerSer | (SEQ.ID.NO.: 31) |
| AsnArgIleThrTyrGln\|SerSerSer | (SEQ.ID.NO.: 32) |
| AsnArgIleSerPheGln\|SerSerSerThr | (SEQ.ID.NO.: 33) |

| | |
|---|---|
| AsnArgIleSerTrpGln\|SerSerSerThr | (SEQ.ID.NO.: 35) |
| AsnArgIleSerTyrGln\|ThrSerSerThr | (SEQ.ID.NO.: 36) |
| AsnLysIleThrTyrGln\|ThrSerSerThr | (SEQ.ID.NO.: 37) |
| AsnLysLeuSerTyrGln\|ThrSerSerThr | (SEQ.ID.NO.: 38) |
| GlnLysLeuSerTyrGln\|SerSerSerThr | (SEQ.ID.NO.: 39) |
| AsnArgLeuSerTyrGln\|ThrSerSerThr | (SEQ.ID.NO.: 40) |
| AsnLysValSerPheGln\|SerSerSerThr | (SEQ.ID.NO.: 41) |
| AsnArgValSerTrpGln\|SerSerSerThr | (SEQ.ID.NO.: 42) |
| GlnLysValSerTyrGln\|SerSerSerThr | (SEQ.ID.NO.: 43) |
| GlnLysIleSerTyrGln\|ThrSerSerThr | (SEQ.ID.NO.: 34) |
| AsnLysIleSerTyrGln\|SerSerSerThr | (SEQ.ID.NO.: 44) |

Similarly, the following oligopeptides may be synthesized by techniques well known to persons of ordinary skill in the art and would be expected to be proteolytically cleaved by free PSA:

| | |
|---|---|
| GlyGluGlnGlyValGlnLysAspValSerGlnSer SerIleTyr\|SerGlnThrGlu, | (SEQ.ID.NO.: 45) |
| GlyGluAsnGlyLeuGlnLysAspValSerGlnSer SerIleTyr\|SerGlnThrGlu, | (SEQ.ID.NO.: 47) |
| GlyGluAsnGlyValAsnLysAspValSerGlnSer SerIleTyr\|SerGlnThrGlu, | (SEQ.ID.NO.: 48) |
| GlyGluAsnGlyValGlnArgAspValSerGlnArg SerIleTyr\|SerGlnThrGlu, | (SEQ.ID.NO.: 49) |
| GlyGluAsnGlyValGlnLysAspValSerGlnLys SerIleTyr\|SerGlnThrGlu, | (SEQ.ID.NO.: 50) |
| GlyGluAsnGlyValGlnLysAspLeuSerGlnThr SerIleTyr\|SerGlnThrGlu, | (SEQ.ID.NO.: 51) |
| GlyGluAsnGlyValGlnLysAspValSerGlnSer SerIlePhe\|SerGlnThrGlu, | (SEQ.ID.NO.: 52) |
| GlyGluAsnGlyValGlnLysAspMetSerGlnSer SerIleTyr\|ThrGlnThrGlu, | (SEQ.ID.NO.: 53) |
| GlyGluAsnGlyValGlnLysAspValSerGlnArg SerIleTyr\|ThrGlnThrGlu, | (SEQ.ID.NO.: 54) |
| GlyGluAsnGlyValGlnLysAspValSerGlnSer SerIleTyr\|SerGlnSerGlu, | (SEQ.ID.NO.: 55) |
| GlyGluAsnGlyValGlnLysAspValSerGlnArg SerIleTyr\|SerAsnThrGlu, | (SEQ.ID.NO.: 56) |
| GlyLysAlaIleSerSerGlnTyr\|SerAsnThrGlu GluArgLeu, | (SEQ.ID.NO.: 57) |
| GlyArgGlyIleSerSerGlnTyr\|SerAsnThrGlu GluArgLeu, | (SEQ.ID.NO.: 59) |
| GlyLysGlyIleThrSerGlnTyr\|SerAsnThrGlu GluArgLeu, | (SEQ.ID.NO.: 60) |
| GlyLysGlyIleSerThrGlnTyr\|SerAsnThrGlu GluArgLeu, | (SEQ.ID.NO.: 61) |
| GlyLysGlyIleSerSerAsnTyr\|SerAsnThrGlu GluArgLeu, | (SEQ.ID.NO.: 62) |
| AlaLysGlyIleSerSerGlnTyr\|SerAsnThrGlu GluArgLeu, | (SEQ.ID.NO.: 63) |
| GlyLysGlyIleSerSerGlnPhe\|SerAsnThrGlu GluArgLeu, | (SEQ.ID.NO.: 64) |
| GlyLysGlyIleSerSerGlnTyr\|ThrAsnThrGlu GluArgLeu, | (SEQ.ID.NO.: 65) |
| GlyLysGlyIleSerSerGlnTyr\|SerAsnSerGlu luArgLeu, and | (SEQ.ID.NO.: 58) |
| GlyLysGlyIleSerSerGlnTyr\|SerAsnThrAsp luArgLeu; | (SEQ.ID.NO.: 46) | and the like.

The inclusion of the symbol "|" within an amino acid sequence indicates the point within that sequence where the oligopeptide is proteolytically cleaved by free PSA.

The invention also concerns a method for assaying proteolytic free PSA activity in a composition. This is an important aspect of the invention in that such an assay system provides one with the ability to measure quantitatively the amount of free PSA present in certain physiological fluids and tissues. Such an assay will also provide not only the ability to follow isolation and purification of free PSA, but also is a basis for a screening assay for inhibitors of the proteolytic activity of free PSA. The assay method generally includes simply determining the ability of a composition suspected of containing enzymatically active free PSA to proteolytically cleave the oligopeptide.

Typically, the assay protocol is carried out using one of the oligopeptides described hereinabove. However, one may find a particular benefit in construction of an assay wherein the oligopeptide containing the cleavage site is labeled so that one can measure the appearance of such a label, for example, a radioactive label, in both the uncleaved oligopeptide and the portion of the oligopeptide remaining after cleavage which contains the label.

The instant invention further relates to a method for identifying compounds (hereinafter referred to as candidate compounds) that will inhibit the proteolytic activity of free PSA. It is contemplated that this screening technique will prove useful in the general identification of any candidate compound that will serve such as an inhibitory purpose, whether or not the candidate compound is proteinaceous or peptidyl in structure.

Thus, the present invention is also directed to a method for determining the ability of a test substance to inhibit the proteolytic activity of free PSA, the method which comprises:

(a) reacting a substrate, wherein the substrate comprises a sequence of amino acids that is recognized and selectively proteolytically cleaved by free prostate specific antigen, with free prostate specific antigen in the presence of a test substance; and (b) detecting whether the substrate has been cleaved, in which the ability of the test substance to inhibit proteolytic activity of prostate specific antigen is indicated by a decrease in the cleavage of the substrate as compared to the cleavage of the substrate in the absence of the test substance.

The candidate screening assay is quite simple to set up and perform, and is related in many ways to the assay discussed above for determining proteolytic activity. Thus, after obtaining a relatively purified preparation of free PSA, one will desire to simply admix a test substance with the proteolytic preparation, preferably under conditions which would allow the PSA to perform its cleavage function but for inclusion of a inhibitory substance. Thus, for example, one will typically desire to include within the admixture an amount of a known oligopeptide having a PSA specific cleavage site, such as those oligopeptides described hereinabove. In this fashion, one can measure the ability of the test substance to reduce cleavage of the oligopeptide relatively in the presence of the test substance.

Accordingly, one will desire to measure or otherwise determine the activity of the free PSA in the absence of the added test substance relative to the activity in the presence of the test substance in order to assess the relative inhibitory capability of the test substance.

The instant invention also relates to novel anti-cancer compositions useful for the treatment of prostate cancer. Such compositions comprise the oligopeptides of the instant invention covalently bonded directly, or through a chemical linker, to a cytotoxic agent. Such a combination of an oligopeptide and cytotoxic agent may be termed a conjugate. Ideally, the cytotoxic activity of the cytotoxic agent is greatly reduced or absent when the oligopeptide containing the PSA proteolytic cleavage site is bonded directly, or through a chemical linker, to the cytotoxic agent and is intact. Also ideally, the cytotoxic activity of the cytotoxic agent increases significantly or returns to the activity of the unmodified cytotoxic agent upon proteolytic cleavage of the attached oligopeptide at the cleavage site. While it is not necessary for practicing this aspect of the invention, the most preferred embodiment of this aspect of the invention is a conjugate wherein the oligopeptide, and the chemical linker if present, are detached from the cytotoxic agent by the proteolytic activity of the free PSA and any other native proteolytic enzymes present in the tissue proximity, thereby releasing unmodified cytotoxic agent into the physiological environment at the place of proteolytic cleavage.

It is understood that the oligopeptide of the instant invention that is conjugated to the cytotoxic agent, whether through a direct covalent bond or through a chemical linker, does not need to be the oligopeptide that has the greatest recognition by free PSA and is most readily proteolytically cleaved by free PSA. Thus, the oligopeptide that is selected for incorporation in such an anti-cancer composition will be chosen both for its selective, proteolytic cleavage by free PSA and for the cytotoxic activity of the cytotoxic agent-proteolytic residue conjugate (or, in what is felt to be an ideal situation, the unmodified cytotoxic agent) which results from such a cleavage.

Because the conjugates of the invention can be used for modifying a given biological response, cytotoxic agent is not to be construed as limited to classical chemical therapeutic agents. For example, the cytotoxic agent may be a protein or polypeptide possessing a desired biological activity. Such proteins may include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

The preferred cytotoxic agents include, in general, alkylating agents, antiproliferative agents, tubulin binding agents and the like. Preferred classes of cytotoxic agents include, for example, the anthracycline family of drugs, the vinca drugs, the mitomycins, the bleomycins, the cytotoxic nucleosides, the pteridine family of drugs, diynenes, and the podophyllotoxins. Particularly useful members of those classes include, for example, doxorubicin, carminomycin, daunorubicin, aminopterin, methotrexate, methopterin, dichloromethotrexate, mitomycin C, porfiromycin, 5-fluorouracil, 6-mercaptopurine, cytosine arabinoside, podophyllotoxin, or podophyllotoxin derivatives such as etoposide or etoposide phosphate, melphalan, vinblastine, vincristine, leurosidine, vindesine, leurosine and the like. Other useful cytotoxic agents include estramustine, cisplatin and cyclophosphamide. One skilled in the art may make chemical modifications to the desired compound in order to make reactions of that compound more convenient for purposes of preparing conjugates of the invention.

A highly preferred group of cytotoxic agents for the present invention include drugs of the following formulae:

THE METHOTREXATE GROUP OF FORMULA (1)

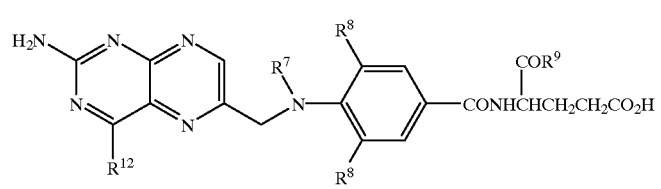

(1)

in which $R^{12}$ is amino or hydroxy;

$R^7$ is hydrogen or methyl;

$R^8$ is hydrogen, fluoro, chloro, bromo or iodo;

$R^9$ is hydroxy or a moiety which completes a salt of the carboxylic acid;

THE MITOMYCIN GROUP OF FORMULA (2)

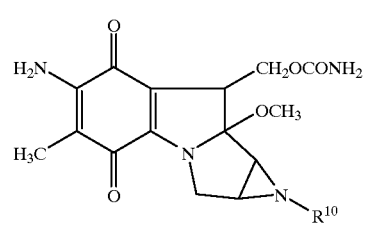

(2)

in which $R^{10}$ is hydrogen or methyl;

THE BLEOMYCIN GROUP OF FORMULA (3)
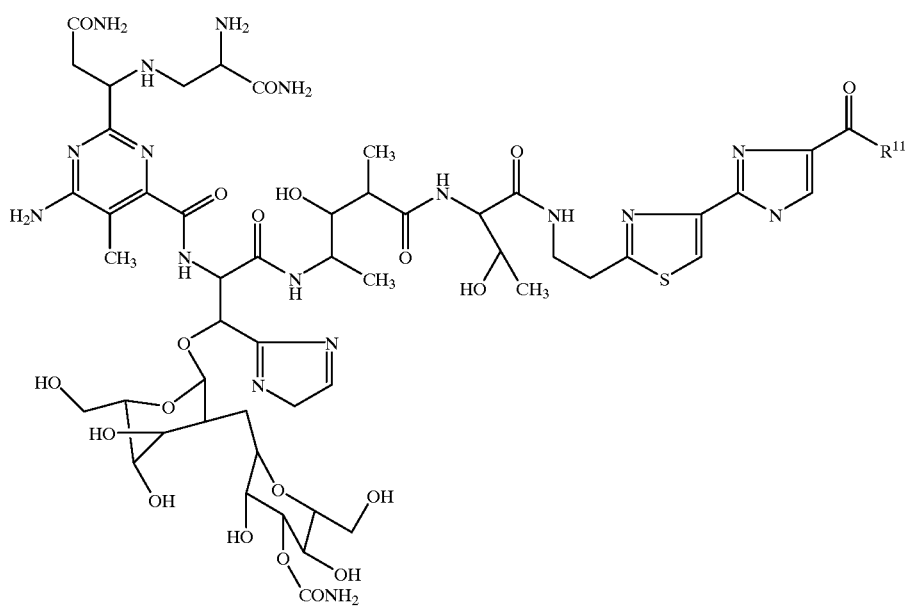
(3)
in which $R^{11}$ is hydroxy, amino, $C_1$–$C_3$ alkylamino, di($C_1$–$C_3$ alkyl)amino, $C_4$–$C_6$ polymethylene amino,
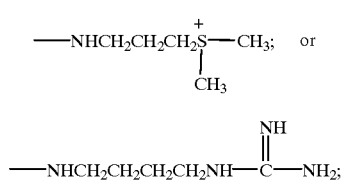
MELPHALAN OF FORMULA (4)
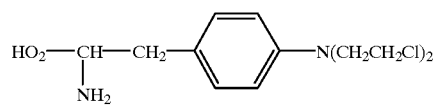
(4)
6-MERCAPTOPURINE OF FORMULA (5)
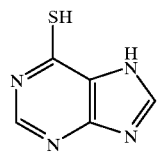
(5)
A CYTOSINE ARABINOSIDE OF FORMULA (6)
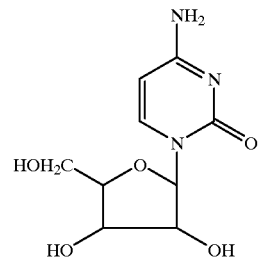
(6)
THE PODOPHYLLOTOXINS OF FORMULA (7)
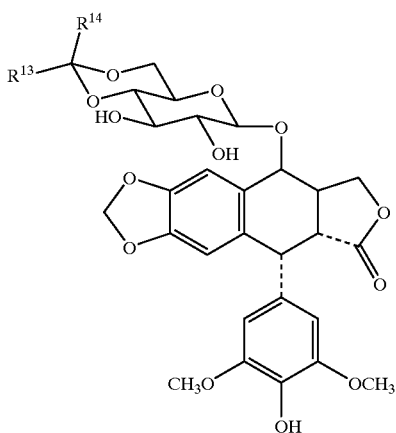
(7)
in which $R^{13}$ is hydrogen or methyl;
$R^{14}$ is methyl or thienyl;
or a phosphate salt thereof;

THE VINCA ALKALOID GROUP OF DRUGS OF FORMULA (8)

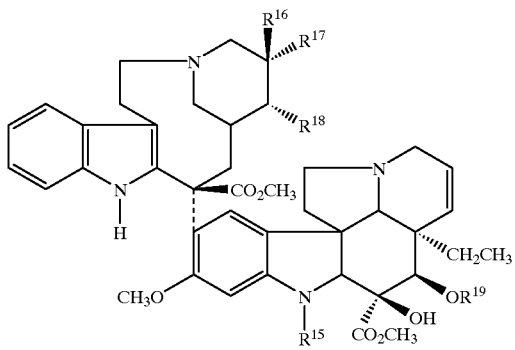

(8)

in which $R^{15}$ is H, $CH_3$ or CHO; when $R^{17}$ and $R^{18}$ are taken singly;

$R^{18}$ is H, and one of $R^{16}$ and $R^{17}$ is ethyl and the other is H or OH; when $R^{17}$ and $R^{18}$ are taken together with the carbons to which they are attached, they form an oxirane ring in which case $R^{16}$ is ethyl;

$R^{19}$ is hydrogen, $(C_1-C_3$ alkyl$)$-CO, or chlorosubstituted $(C_1-C_3$ alkyl$)$-CO;

DIFLUORONUCLEOSIDES OF FORMULA (9)

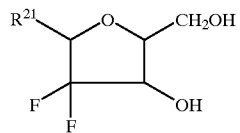

(9)

in which $R^{21}$ is a base of one of the formulae:

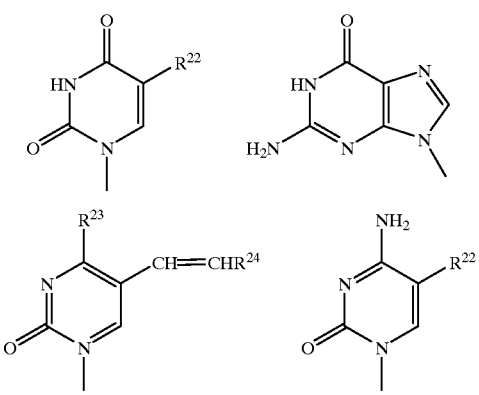

-continued

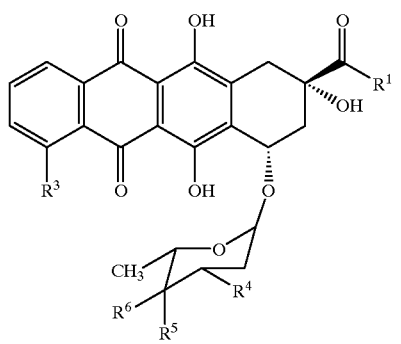

in which $R^{22}$ is hydrogen, methyl, bromo, fluoro, chloro or iodo;
$R^{23}$ is —OH or —$NH_2$;
$R^{24}$ is hydrogen, bromo, chloro or iodo; or,

THE ANTHRACYCLINES ANTIBIOTICS OF FORMULA (10)

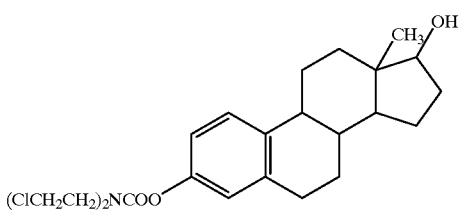

(10)

wherein $R^1$ is —$CH_3$, —$CH_2OH$, —$CH_2OCO(CH_2)_3CH_3$, or —$CH_2OCOCH(OC_2H_5)_2$;

$R^3$ is —$OCH_3$, —OH or —H;

$R^4$ is —$NH_2$, —$NHCOCF_3$, 4-morpholinyl, 3-cyano-4-morpholinyl, 1-piperidinyl, 4-methoxy-1-piperidinyl, benzylamine, dibenzylamine, cyanomethylamine, or 1-cyano-2-methoxyethyl amine;

$R^5$ is —OH —OTHP or —H; and $R^6$ is —OH or —H provided that $R^6$ is not —OH when $R^5$ is —OH or —OTHP.

ESTRAMUSTINE (11)

(11)

[Estramustine structure with (ClCH$_2$CH$_2$)$_2$NCOO— group]

CYCLOPHOSPHAMIDE (12)

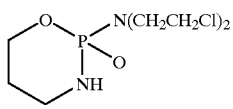

The most highly preferred drugs are the anthracycline antiobiotic agents of Formula (10), described previously. One skilled in the art understands that this structural formula includes compounds which are drugs, or are derivatives of drugs, which have acquired in the art different generic or trivial names. Table 1, which follows, represents a number of anthracycline drugs and their generic or trivial names and which are especially preferred for use in the present invention.

TABLE 1

(11)

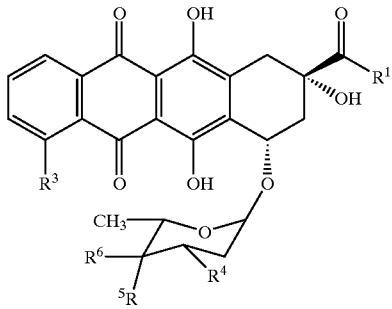

| Compound | $R_1$ | $R_3$ | $R_4$ | $R_5$ | $R_6$ |
|---|---|---|---|---|---|
| daunorubicin[a] | $CH_3$ | $OCH_3$ | $NH_2$ | OH | 4H |
| doxorubicin[b] | $CH_2OH$ | $OCH_3$ | $NH_2$ | OH | H |
| detorubicin | $CH_2OCOCH(OC_2H_5)_2$ | $OCH_3$ | $NH_2$ | OH | H |
| carminomycin | $CH_3$ | OH | $NH_2$ | OH | H |
| idarubicin | $CH_3$ | H | $NH_2$ | OH | H |
| epirubicin | $CH_2OH$ | $OCH_3$ | $NH_2$ | OH | OH |
| esorubicin | $CH_2OH$ | $OCH_3$ | $NH_2$ | H | |
| THP | $CH_2OH$ | $OCH_3$ | $NH_2$ | OTHP | H |
| AD-32 | $CH_2OCO(CH_2)_3CH_3$ | $OCH_3$ | $NHCOCF_3$ | OH | H |

[a]"daunomycin" is an alternative name for daunorubicin
[b]"adriamycin" is an alternative name for doxorubicin Of the compounds shown in Table 1, the most highly preferred drug is doxorubicin. Doxorubicin (also referred to herein as "DOX") is that anthracycline of Formula (10) in which $R_1$ is —$CH_2OH$, $R_3$ is —$OCH_3$, $R_4$ is —$NH_2$, $R_5$ is —OH, and $R_6$ is —H.

The oligopeptides, peptide subunits and peptide derivatives (also termed "peptides") of the present invention can be synthesized from their constituent amino acids by conventional peptide synthesis techniques, preferably by solid-phase technology. The peptides are then purified by reverse-phase high performance liquid chromatography (HPLC).

Standard methods of peptide synthesis are disclosed, for example, in the following works: Schroeder et al., "The Peptides", Vol. I, Academic Press 1965; Bodansky et al., "Peptide Synthesis", Interscience Publishers, 1966; McOmie (ed.) "Protective Groups in Organic Chemistry", Plenum Press, 1973; Barany et al., "The Peptides: Analysis, Synthesis, Biology" 2, Chapter 1, Academic Press, 1980, and Stewart et al., "*Solid Phase Peptide Synthesis*", Second Edition, Pierce Chemical Company, 1984. The teachings of these works are hereby incorporated by reference.

The conjugates of the instant invention which comprise the oligopeptide containing the PSA cleavage site and a cytotoxic agent may similarly be synthesized by techniques well known in the medicinal chemistry art. For example, a free amine moiety on the cytotoxic agent may be covalently attached to the oligopeptide at the carboxyl terminus such that an amide bond is formed. Similarly, an amide bond may be formed by covalently coupling an amine moiety of the oligopeptide and a carboxyl moiety of the cytotoxic agent. For these purposes a reagent such as a combination of 2-(1H-benzotriazol-1-yl)-1,3,3-tetramethyluronium hexafluorophosphate (known as HBTU) and 1-hyroxybenzotriazole hydrate known as HOBT), dicyclohexylcarbodiimide (DCC), N-ethyl-N-(3-dimethylaminopropyl)-carbodiimide (EDC), diphenylphosphorylazide (DPPA), benzotriazol-1-yl-oxy-tris(dimethylamino)phosphonium hexafluorophosphate (BOP) and the like may be utilized.

Furthermore, the instant conjugate may be formed by a non-peptidyl bond between the PSA cleavage site and a cytotoxic agent. For example, the cytotoxic agent may be covalently attached to the carboxyl terminus of the oligopeptide via a hydroxyl moiety on the cytotoxic agent, thereby forming an ester linkage. For this purpose a reagent such as a combination of HBTU and HOBT, a combination of BOP and imidazole, a combination of DCC and DMAP, and the like may be utilized. The carboxylic acid may also be activated by forming the nitrophenyl ester or the like and reacted in the presence of DBU (1,8-diazabicyclo[5,4,0]undec-7-ene.

The instant conjugate may also be formed by attachment of the oligopeptide to the cytotoxic agent via a linker unit. Such linker units include, for example, a biscarbonyl alkyl diradical whereby an amine moiety on the cytotoxic agent is connected with the linker unit to form an amide bond and the amino terminus of the oligopeptide is connected with the other end of the linker unit also forming an amide bond. Other such linker units which are stable to the physiological environment when not in the presence of free PSA, but are cleavable upon the cleavage of the PSA proteolytic cleavage site, are also envisioned. Furthermore, linker units may be utilized that, upon cleavage of the PSA proteolytic cleavage site, remain attached to the cytotoxic agent but do not significantly decrease the cytotoxic activity of such a post-cleavage cytotoxic agent derivative when compared with an unmodified cytotoxic agent.

One skilled in the art understands that in the synthesis of compounds of the invention, one may need to protect or block various reactive functionalities on the starting compounds and intermediates while a desired reaction is carried out on other portions of the molecule. After the desired reactions are complete, or at any desired time, normally such protecting groups will be removed by, for example, hydrolytic or hydrogenolytic means. Such protection and deprotection steps are conventional in organic chemistry. One skilled in the art is referred to *Protective Groups in Organic Chemistry,* McOmie, ed., Plenum Press, NY, N.Y. (1973); and, *Protective Groups in Organic Synthesis,* Greene, ed., John Wiley & Sons, NY, N.Y. (1981) for the teaching of protective groups which may be useful in the preparation of compounds of the present invention.

By way of example only, useful amino-protecting groups may include, for example, $C_1$–$C_{10}$ alkanoyl groups such as formyl, acetyl, dichloroacetyl, propionyl, hexanoyl, 3,3-diethylhexanoyl, γ-chlorobutryl, and the like; $C_1$–$C_{10}$ alkoxycarbonyl and $C_5$–$C_{15}$ aryloxycarbonyl groups such as tert-butoxycarbonyl, benzyloxycarbonyl, allyloxycarbonyl, 4-nitrobenzyloxycarbonyl, fluorenylmethyloxycarbonyl and cinnamoyloxycarbonyl; halo-($C_1$–$C_{10}$)-alkoxycarbonyl such as 2,2,2-trichloroethoxycarbonyl; and $C_1$–$C_{15}$ arylalkyl and alkenyl group such as benzyl, phenethyl, allyl, trityl, and the like. Other commonly used amino-protecting groups are those in the form of enamines prepared with β-keto-esters such as methyl or ethyl acetoacetate.

Useful carboxy-protecting groups may include, for example, $C_1$–$C_{10}$ alkyl groups such as methyl, tert-butyl, decyl; halo-$C_1$–$C_{10}$ alkyl such as 2,2,2-trichloroethyl, and 2-iodoethyl; $C_5$–$C_{15}$ arylalkyl such as benzyl, 4-methoxybenzyl, 4-nitrobenzyl, triphenylmethyl, diphenylmethyl; $C_1$–$C_{10}$ alkanoyloxymethyl such as acetoxymethyl, propionoxymethyl and the like; and groups such as phenacyl, 4-halophenacyl, allyl, dimethylallyl, tri-($C_1$–$C_3$ alkyl)silyl, such as trimethylsilyl, β-p-toluenesulfonylethyl, β-p-nitrophenyl-thioethyl, 2,4,6-trimethylbenzyl, β-methylthioethyl, phthalimidomethyl, 2,4-dinitrophenylsulphenyl, 2-nitrobenzhydryl and related groups.

Similarly, useful hydroxy protecting groups may include, for example, the formyl group, the chloroacetyl group, the benzyl group, the benzhydryl group, the trityl group, the 4-nitrobenzyl group, the trimethylsilyl group, the phenacyl group, the tert-butyl group, the methoxymethyl group, the tetrahydropyranyl group, and the like.

With respect to the preferred embodiment of an oligopeptide combined with the anthracycline antibiotic doxorubicin, the following Reaction Schemes illustrate the synthsis of the conjugates of the instant invention.

REACTION SCHEME I

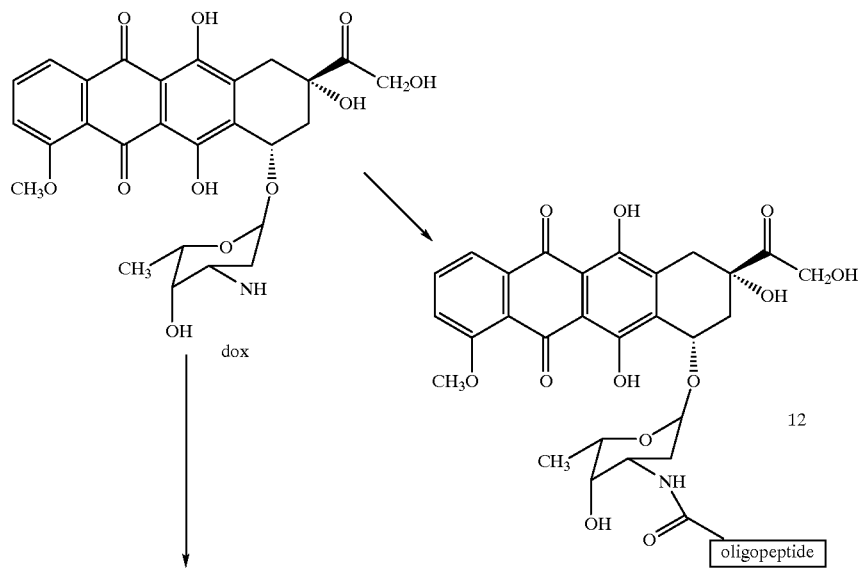

-continued
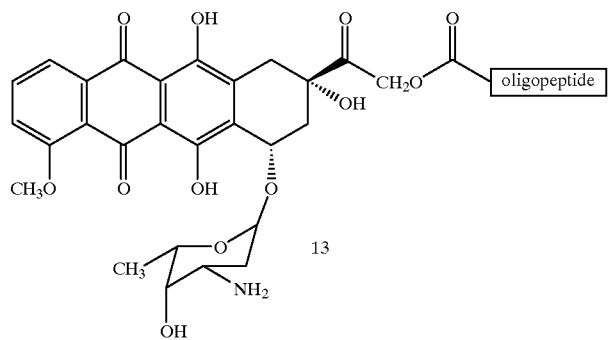
REACTION SCHEME II
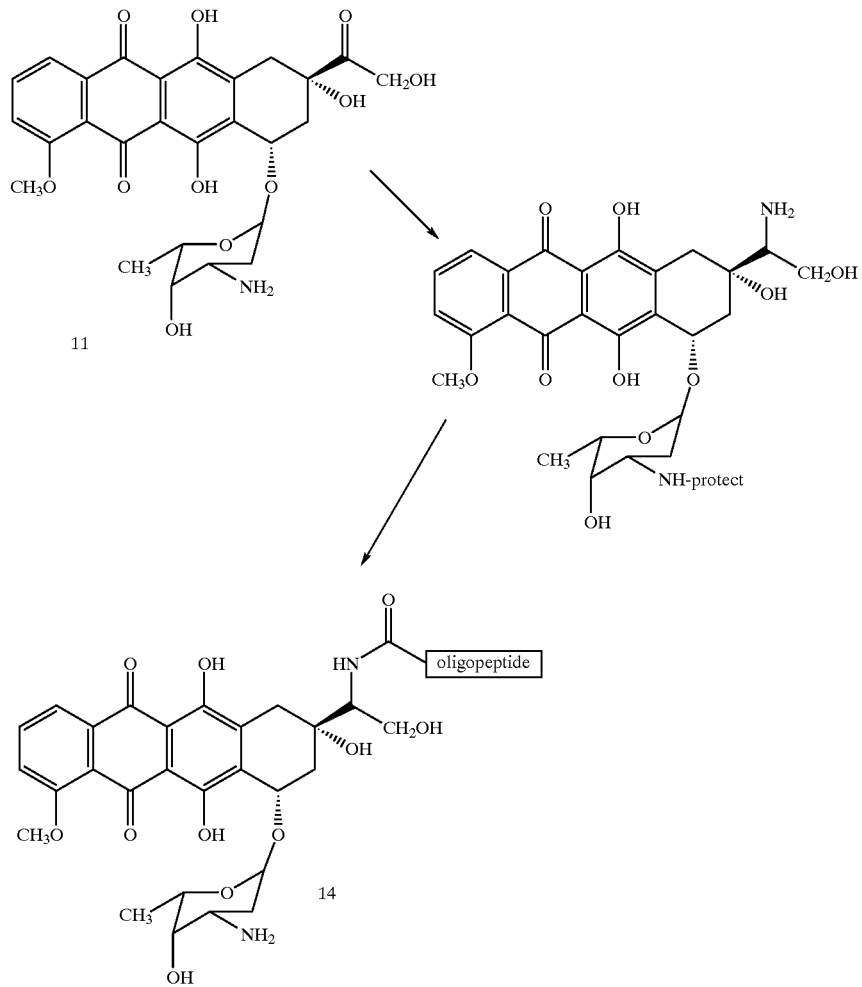

REACTION SCHEME III
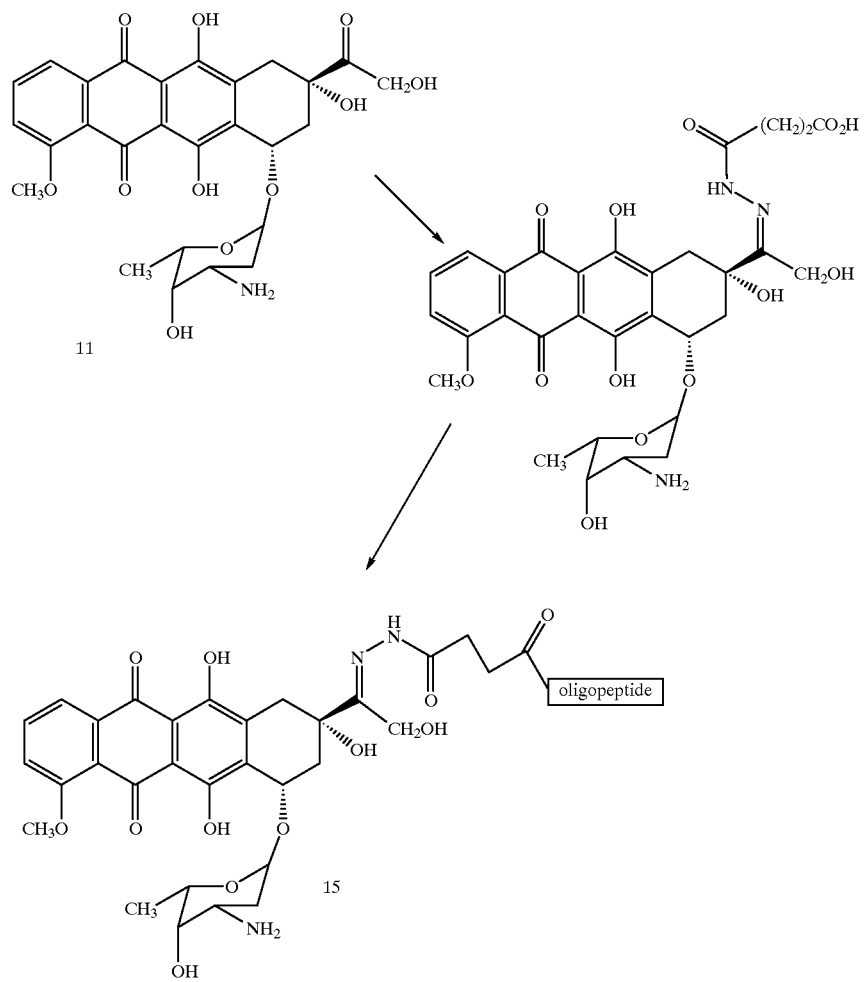
REACTION SCHEME IV
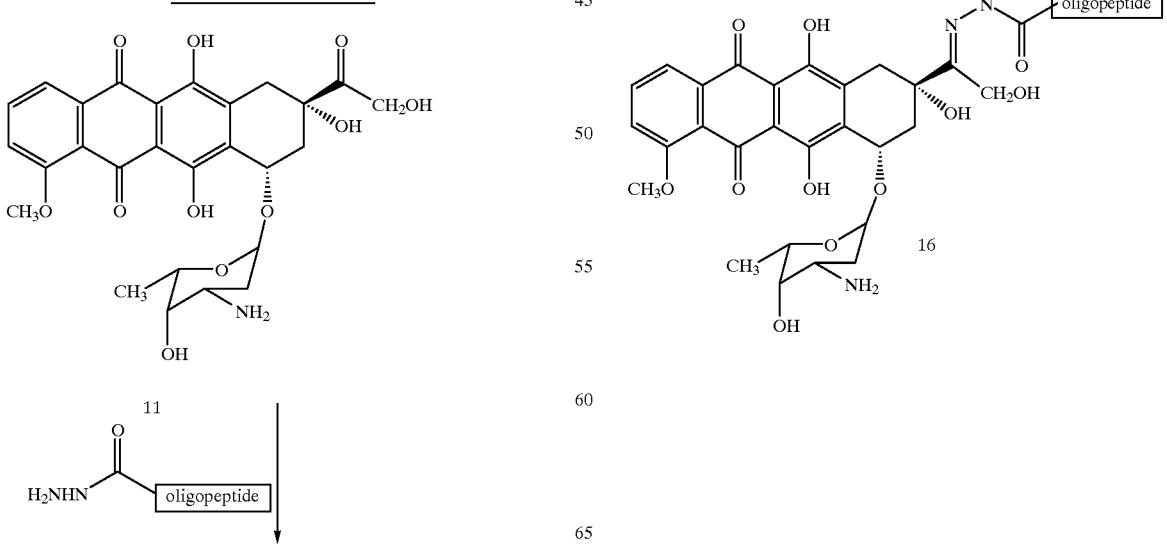
-continued

REACTION SCHEME V

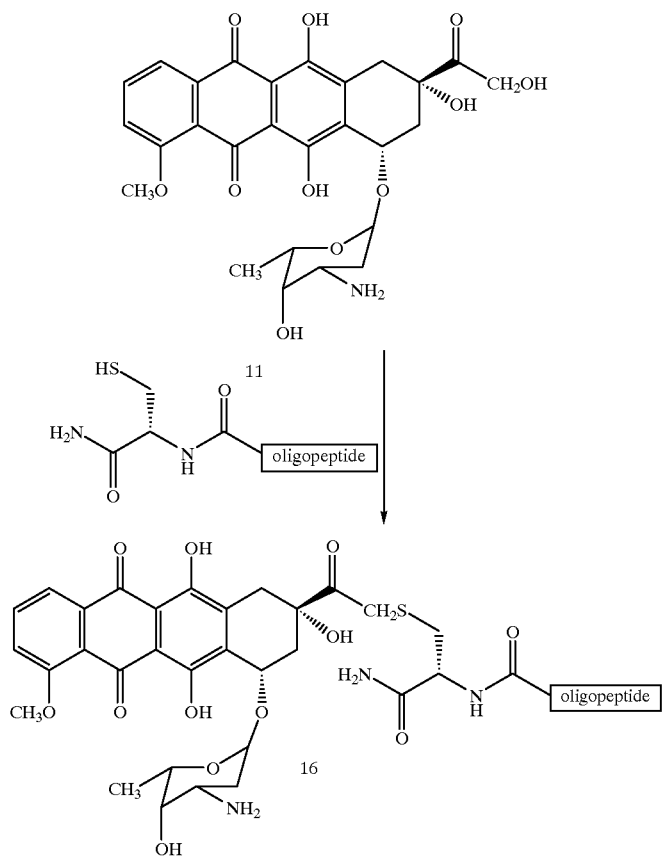

Reaction Scheme VI illustrates preparation of conjugates of the oligopeptides of the instant invention and the vinca alkaloid cytotoxic agent vinblastine. Attachement of the N-terminus of the oligopeptide to vinblastine is illustrated (S. P. Kandukuri et al. J. Med. Chem. 28:1079–1088 (1985)). However, conjugation of the oligopeptide at other positions and functional groups of vinblastine and at the C-terminus of the oligopeptide is also expected to provide compounds useful in the treatment of prostate cancer.

It is also understood that conjugates may be prepared wherein the N-terminus of the oligopeptide of the instant invention is covalently attached to one cytotoxic agent, such as vinblastine, while the C-terminus is simultaneously attached to another cytotoxic agent, which is the same or different cytotoxic agent, such as doxorubicin. Such a poly-cytotoxic conjugate may offer advantages over a conjugate containing only one cytotoxic agent.

REACTION SCHEME VI

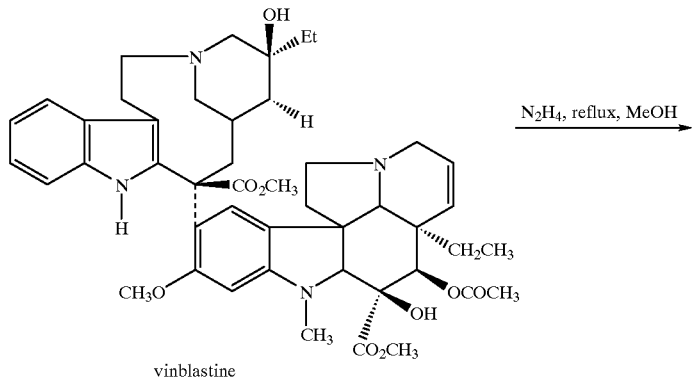

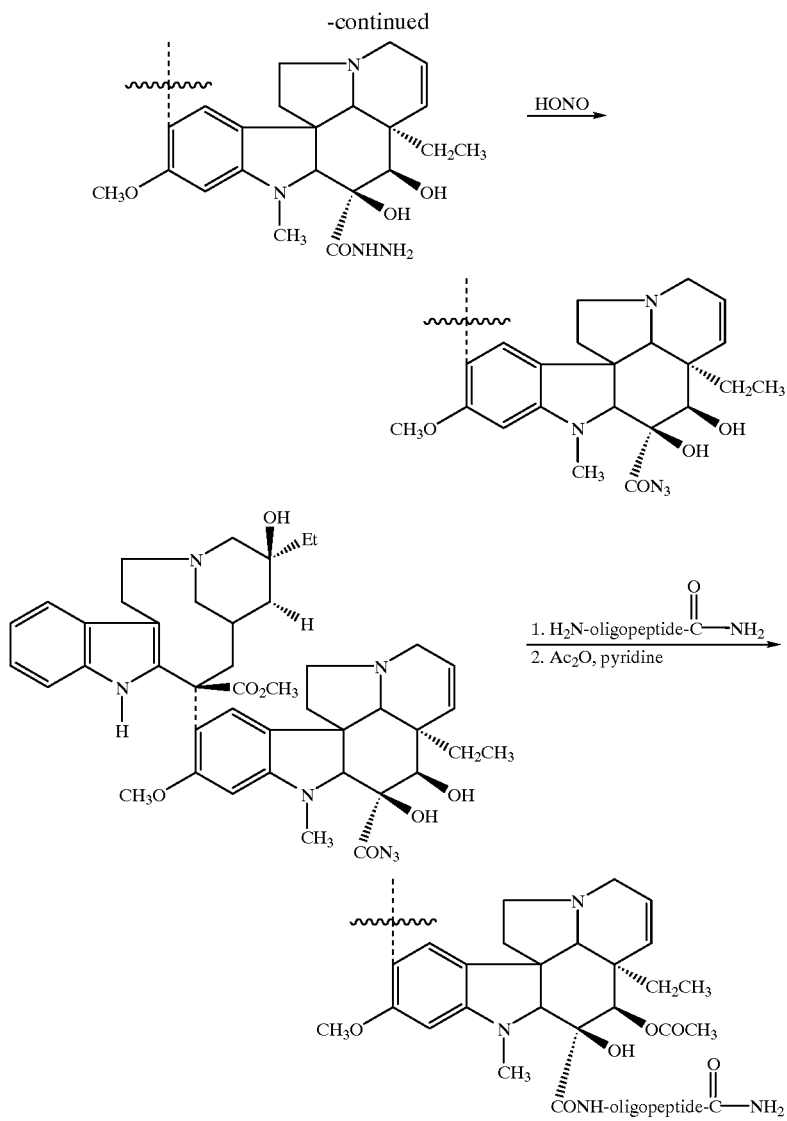

The oligopeptide-cytotoxic agent conjugate of the instant invention wherein the cytotoxic agent is the preferred cytotoxic agent doxorubicin may be described by the general formula I below:

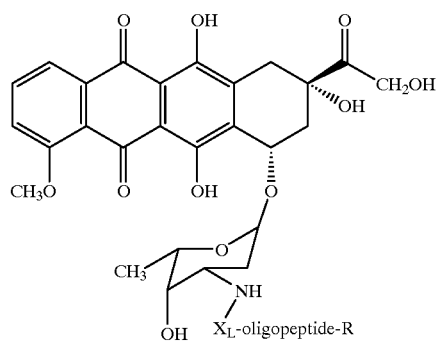

wherein:
oligopeptide is an oligopeptide which is specifically recognized by the free prostate specific antigen (PSA) and is capable of being proteolytically cleaved by the enzymatic activity of the free prostate specific antigen;

$X_L$ is absent or is an amino acid selected from:
a) phenylalanine,
b) leucine,
c) valine,
d) isoleucine,
e) (2-naphthyl)alanine,
f) cyclohexylalanine,
g) diphenylalanine,
h) norvaline, and
j) norleucine;

R is hydrogen or —(C=O)$R^1$; and
$R^1$ is $C_1$–$C_6$-alkyl or aryl.

In a preferred embodiment of the oligopeptide-cytotoxic agent conjugate:
oligopeptide is an oligomer that comprises an amino acid sequence selected from:
a) AsnLysIleSerTyrGln|Ser (SEQ.ID.NO.: 13),
b) LysIleSerTyrGln|Ser (SEQ.ID.NO.: 14),
c) GlyGluAsnGlyValGlnLysAspValSerGlnXaa
SerIleTyr|SerGlnThrGlu (SEQ.ID.NO.: 15), d) GlyLysGlyIleSerSerGlnTyr|SerAsnThrGluGluArgLeu (SEQ.ID.NO.: 2),
e) AsnLysIleSerTyrTyr|Ser (SEQ.ID.NO.: 127),
f) AsnLysAlaSerTyrGln|Ser (SEQ.ID.NO.: 128),
g) SerTyrGln|SerSer (SEQ.ID.NO.: 129), and
h) hArgTyrGln|SerSer (SEQ.ID.NO.: 141);

wherein Xaa is any natural amino acid;

$X_L$ is absent or is an amino acid selected from:
  a) leucine,
  b) isoleucine,
  c) norleucine, and
  d) valine; and R is acetyl, pivaloyl or benzoyl.

The following compounds are specific examples of the oligopeptide-cytotoxic agent conjugate of the instant invention:

[Chemical structure of doxorubicin-like compound with CH₃O, OH, CH₂OH, CH₃, NH-X substituents]

wherein X is:

(SEQ.ID.NO.:13)
H₂N—AsnLysIleSerTyrGlnSer-C(=O)—, (SEQ.ID.NO.:16)
H₂N—AsnLysIleSerTyrGlnSerSer-C(=O)—, (SEQ.ID.NO.:17)
H₂N—AsnLysIleSerTyrGlnSerSerSer-C(=O)—, (SEQ.ID.NO.:10)
H₂N—AsnLysIleSerTyrGlnSerSerThr-C(=O)—, (SEQ.ID.NO.:3)
H₂N—AsnLysIleSerTyrGlnSerSerThrGlu-C(=O)—, (SEQ.ID.NO.:11)
H₂N—AlaAsnLysIleSerTyrGlnSerSerThrGlu-C(=O)—, (SEQ.ID.NO.:117)
AcHN—AlaAsnLysIleSerTyrGlnSerSerSerThr-C(=O)—, (SEQ.ID.NO.:70)
AcHN—AlaAsnLysIleSerTyrGlnSerSerSerThrLeu-C(=O)—, (SEQ.ID.NO.:118)
AcHN—AlaAsnLysAlaSerTyrGlnSerAlaSerThrLeu-C(=O)—, (SEQ.ID.NO.:119)
AcHN—AlaAsnLysAlaSerTyrGlnSerAlaSerLeu-C(=O)—, (SEQ.ID.NO.:120)
AcHN—AlaAsnLysAlaSerTyrGlnSerSerSerLeu-C(=O)—, (SEQ.ID.NO.:121)
AcHN—AlaAsnLysAlaSerTyrGlnSerSerLeu-C(=O)—, (SEQ.ID.NO.:144)
AcHN—SerTyrGlnSerSerSerLeu-C(=O)—, (SEQ.ID.NO.:145)
AcHN—hArgTyrGlnSerSerSerLeu-C(=O)—, (SEQ.ID.NO.:124)
AcHN—LysTyrGlnSerSerSerLeu-C(=O)—, or (SEQ.ID.NO.:146)
AcHN—LysTyrGlnSerSerNle-C(=O)—.

It is well known in the art, and understood in the instant invention, that peptidyl therapeutic agents such as the instant oligopeptide-cytotoxic agent conjugates preferably have the terminal amino moiety of any oligopeptide substituent protected with a suitable protecting group, such as acetyl, benzoyl, pivaloyl and the like. Such protection of the terminal amino group reduces or eliminates the enzymatic degradation of such peptidyl therapeutic agents by the action of exogenous amino peptidases which are present in the blood plasma of warm blooded animals.

The oligopeptide-cytotoxic agent conjugates of the invention are administered to the patient in the form of a pharmaceutical composition which comprises a conjugate of Formula (I) and a pharmaceutically acceptable carrier, excipient or diluent therefor. As used, "pharmaceutically acceptable" refers to those agents which are useful in the treatment or diagnosis of a warm-blooded animal including, for example, a human, equine, procine, bovine, murine, canine, feline, or other mammal, as well as an avian or other warm-blooded animal. The preferred mode of administration is parenterally, particularly by the intravenous, intramuscular, subcutaneous, intraperitoneal, or intralymphatic route. Such formulations can be prepared using carriers, diluents or excipients familiar to one skilled in the art. In this regard, See, e.g. *Remington's Pharmaceutical Sciences,* 16th ed., 1980, Mack Publishing Company, edited by Osol et al. Such compositions may include proteins, such as serum proteins, for example, human serum albumin, buffers or buffering substances such as phosphates, other salts, or electrolytes, and the like. Suitable diluents may include, for example, sterile water, isotonic saline, dilute aqueous dextrose, a polyhydric alcohol or mixtures of such alcohols, for example, glycerin, propylene glycol, polyethylene glycol and the like. The compositions may contain preservatives such as phenethyl alcohol, methyl and propyl parabens, thimerosal, and the like. If desired, the composition can include about 0.05 to about 0.20 percent by weight of an antioxidant such as sodium metabisulfite or sodium bisulfite.

For intravenous administration, the composition preferably will be prepared so that the amount administered to the patient will be from about 0.01 to about 1 g of the conjugate. Preferably, the amount administered will be in the range of about 0.2 g to about 1 g of the conjugate. The conjugates of the invention are effective over a wide dosage range depending on factors such as the disease state to be treated or the biological effect to be modified, the manner in which the conjugate is administered, the age, weight and condition of the patient as well as other factors to be determined by the treating physician. Thus, the amount administered to any given patient must be determined on an individual basis.

One skilled in the art will appreciate that although specific reagents and reaction conditions are outlined in the following examples, modification can be made which are meant to be encompassed by the spirit and scope of the invention. The following preparations and examples, therefore, are provided to further illustrate the invention, and are not limiting.

EXAMPLES

EXAMPLE 1

Identification of the Semenogelin PSA Mediated Cleavage Site

Liquefaction of the seminal gel parallels proteolytic fragmentation of semenogelin I [Lilja, H., Laurell, C. B., (1984) Scand. J. Clin. Lab. Inves. 44, 447–452]. It is believed that the proteolytic fragmentation of semenogelin is mainly due to the proteolytic activity of prostate-specific antigen [Lilja, H., (1985) J. Clin. Invest. 76, 1899–1903]. Utilizing the published sequence of semenogelin I [Lilja, H., Abrahamsson, P. A., Lundwall, A., (1989) J. of Biol. Chem. 264, 1894–1900] (FIG. 1) we designed polymerase chain reaction primers to clone the semenogelin cDNA from a commercially available prostatic cDNA library (Clonetech, Palo Alto, Calif.). The purified semenogelin cDNA was placed into the bacterial expression vector pTAC [Linemeyer, D. L., Kelly, L. J., Minke, J. G., Gimenez-Gallego, G., DeSalvo, J. and Thomas, K. A., (1987) Bio/Technology 5, 960–965]. The semenogelin cDNA was designed so that a tubulin epitope was placed at the carboxyl end of semenogelin protein. The bacterially expressed semenogelin protein was purified on an anti-tubulin antibody column. The purified semenogelin I protein was mixed with commercially prepared prostate-specific antigen (PSA) (York Biologicals International, Stony Brook, N.Y.) in an 100 to 1 molar ratio (semenogelin I/PSA) in 12 mM Tris pH 8.0, 25 mM NaCl, 0.5 mM $CaCl_2$, and incubated for various times. The digest was fractionated by polyacrylamide gel electrophoresis and transferred by electrophoresis to ProBlott filter paper (Applied Biosystems, Inc., Foster City, Calif.) in CAPS buffer [Matsudaira, P., (1987) J. Biol. Chem. 252, 10035–10038]. The ProBlott filter paper was stained with coomassie blue to identify the novel PSA generated semenogelin I protein fragments. The novel fragments were cut out of the filter with a scalpel and submitted for sequence determination. After the proteolytic fragments were identified by variable time digestion, a 10 minute digestion reaction was performed. The affinity of PSA for the 5 potential cleavage sites in semenogelin I was determined to be as follows: site 349/350>site 375/376>site 289/290=site 315/316>site 159/160. The relative affinities were derived from the comassie blue staining intensity of each PSA generated peptide fragment. These intensities had approximate ratios of 3:1:0.6:0.3.

EXAMPLE 2

Preparation of Oligopeptides which Comprise the PSA Mediated Cleavage Site

Oligopeptides were prepared by solid-phase synthesis, using a double coupling protocol for the introduction of amino acids on the Applied Biosystems model 430A automated peptide synthesizer. Deprotection and removal of the oligopeptide from the resin support were achieved by treatment with liquid hydrofluoric acid. The oligopeptides were purified by preparative high pressure liquid chromatography on reverse phase C18 silica columns using an aqueous 0.1 % trifluoroacetic acid/acetonitrile gradient. Identity and homogeneity of the oligopeptides were confirmed by amino acid composition analysis, high pressure liquid chromatography, and fast atom bombardment mass spectral analysis. The oligopeptides that were prepared by this method are shown in FIG. 2.

EXAMPLE 3

Assessment of the Recognition of Oligopeptides by Free PSA

The oligopeptides prepared as described in Example 2 were individually dissolved in PSA digestion buffer (12 mM tris(hydroxymethyl)aminomethane pH8.0, 25 mM NaCl, 0.5 mM $CaCl_2$) and the solution added to PSA at a molar ration of 100 to 1. The reaction is quenched after various reaction times by the addition of trifluoroacetic acid (TFA) to a final 1% (volume/volume). The quenched reaction was analyzed by HPLC on a reversed-phase C18 column using an aqueous 0.1% TFA/acetonitrile gradient. The results of the assessment are shown in FIG. 2. Other oligopeptides prepared as described in Example 2 were tested in the same assay wherein the reaction was quenched at 4 hours. Those results of the assessment are shown in FIG. 3. The removal of an asparagine residue from the amino terminus of the oligopeptide results in a significant loss of PSA mediated peptide hydrolysis, while the presence of a glutamic acid residue at the carboxyl end of the peptide appears not to be essential to recognition by PSA.

EXAMPLE 4

Preparation of Non-cleavable Oligopeptide-Doxorubicin Conjugates

The derivatives of doxorubicin shown in Table 2 were prepared using the following general reaction: To a mixture of doxorubicin (Sigma) and the corresponding peptide (prepared by solid phase synthesis or commercially available (Sigma)) in DMSO was added HBTU and HOBT along with diisopropylethylamine and the reaction mixture was stirred overnight. The crude reaction mixture was purified directly by preparative HPLC on a reversed-phase C-18 column using a 0.1% trifluoroacetic acid (TFA) in acetonitrile/0.1% TFA in water gradient.

TABLE 2

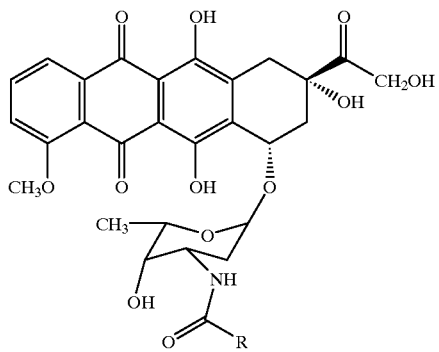

| Compound | R | MS (parent ion) |
|---|---|---|
| 12a | Ala-H | 615 |
| 12b | Ala-N-Ac | 657 |
| 12c | Ala-Ala-Ala-N-Ac | 799.5 |
| 12d | Ala-Ser-Ala-Gly-Thr-Pro-Gly-Ala-N-Ac (SEQ.ID.NO.: 12) | 1199 |

EXAMPLE 5

In vitro Assay of Cytotoxicity of Peptidyl Derivatives of Doxorubicin

The cytotoxicities of the non-cleaveable oligopeptide-doxorubicin conjugates, prepared as described in Example 4, against a line of cells which is known to be killed by unmodified doxorubicin were assessed with an Alamar Blue assay. Specifically, cell cultures of LNCaP prostate tumor cells, which are a human metastatic prostate adenocarcinoma isolated from a needle biopsy of a lymph node (LNCaP.FGC: American Type Culture Collection, ATCC CRL 1740), or DuPRO cells in 96 well plates were diluted with medium containing various concentrations of a given conjugate (final plate well volume of 200 μl). The cells were incubated for 3 days at 37° C. and then 20 μl of Alamar Blue was added to the assay well. The cells were further incubated and the assay plates were read on a EL-310 ELISA reader at the dual wavelengths of 570 and 600 nm at 4 and 7 hours after addition of Alamar Blue. Relative percentage viability at the various concentration of conjugate tested was then calculated versus control (no conjugate) cultures. Cytotoxicities of unmodified doxorubicin and unmodified oligopeptide were also assessed. FIG. 3 shows the cytotoxicity data for a representative compound (Compound 12d).

EXAMPLE 6

Assessment of Enzymatically Active PSA from LNCaP Cells

Enzymatic activity was demonstrated by incubating LNCaP serum free media (concentrated approximately 200 fold) with recombinant Senemogelin I protein. Approximately 0.5 μg of immunologically reactive PSA in concentrated conditioned media [determined by HYBRIDTECH (Tandem E) elisa] was mixed with approximately 3 μg of recombinant Semenogelin I and incubated for 4 hours at 37° C. At the end of the incubation, the digest mixture was analyzed by Western blot procedures. The results show that purified PSA from semen and PSA from LNCaP conditioned media generate identical proteolytic maps of the recombinant Semenogelin I protein. Thus, LNCap cells produce enzymatically active PSA. LNCaP are tumorigenic in nude mice and produce detectable levels of circulating PSA.

EXAMPLE 7

Preparation of Cleavable Oligopeptide-Doxorubicin Conjugates

The derivatives of doxorubicin wherein an oligopeptide which is proteolytically cleaved by free PSA is covalently attached to the amine of the sugar moiety of the doxorubicin were prepared using the following general reaction: To a mixture of doxorubicin (Sigma) and the corresponding peptide (prepared by solid phase synthesis as described in Example 2) in DMSO was added HBTU and HOBT along with diisopropylethylamine and the reaction mixture stirred overnight. The crude reaction mixture was purified directly by preparative HPLC on a reversed-phase C-18 column using a 0.1% trifluoroacetic acid (TFA) in acetonitrile/0.1% TFA in water gradient. When reactive amine moieties were present on the peptide, such a functionality was typically protected as the fluorenylmethyloxycarbonyl adduct, which was removed by treatment with a secondary amine, such as piperidine and the like, subsequent to conjugation with doxirubicin. The instant conjugates have a structure of the general formula

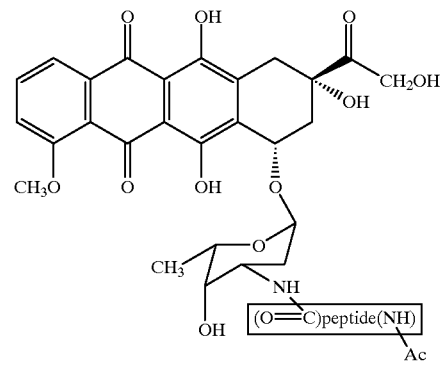

and may be represented by the phrase "Ac-peptide-DOX (3')." Conjugates prepared by this method are listed in FIG. 5.

EXAMPLE 8

Assessment of the Recognition of Oligopeptide-Doxorubicin Conjugates by Free PSA The conjugates prepared as described in Example 7 were individually dissolved in PSA digestion buffer (12 mM tris(hydroxymethyl)aminomethane pH8.0, 25 mM NaCl, 0.5 mM $CaCl_2$) and the solution added to PSA at a molar ration of 100 to 1. The reaction is quenched after various reaction times by the addition of trifluoroacetic acid (TFA) to a final 1% (volume/volume). The quenched reaction was analyzed by HPLC on a reversed-phase C18 column using an aqueous 0.1% TFA/acetonitrile gradient. The results of the assessment are shown in FIG. 5.

EXAMPLE 9

Assessment of the Cleavage of Oligopeptide-Doxorubicin Conjugates in Cell Conditioned Media Cell conditioned serum-free MEMα media (phenol red minus) was collected 3 days after the addition of the media to either LNCap or Dupro (prepared as described in *J. Urology,* 146:915–919 (1991)) cell lines. The media was concentrated 20 fold using an Amicon® Centriprep™ concentrator with a 10,000 molecular weight cutoff. The LNCap conditioned media contained free PSA protein at, on average, approximately 100 ng/mL concentration as determined by the Tandem®-E PSA immunodetection kit (Hybritech®). There was no detectable free PSA in the Dupro cell conditioned media.

100 μL portions of concentrated conditioned media was mixed with 35 μg of a oligopeptide-doxorubicin conjugate prepared as described in Example 7 and the mixture was incubated at 37° C. for 0, 4 and 24 hour time points. The reactions were stopped by the addition of $ZnCl_2$ (to a 0.01M final concentration and analyzed by HPLC on a reversed-phase C18 column using an aqueous 0.1% TFA/acetonitrile gradient to determine the percentage of peptide-cytotoxic agent conjugate that had been digested. The results of the assessment are shown in FIG. 6.

EXAMPLE 10

In vitro Assay of Cytotoxicity of Peptidyl Derivatives of Doxorubicin

The cytotoxicities of the cleaveable oligopeptide-doxorubicin conjugates, prepared as described in Example 7, against a line of cells which is known to be killed by unmodified doxorubicin was assessed with an Alamar Blue assay as described in Example 5. Specifically, cell cultures of LNCap prostate tumor cells or DuPRO cells in 96 well plates was diluted with medium containing various concentrations of a given conjugate (final plate well volume of 200 μl). The cells were incubated for 3 days at 37° C., 20 μl of Alamar Blue is added to the assay well. The cells were further incubated and the assay plates were read on a EL-310 ELISA reader at the dual wavelengths of 570 and 600 nm at 4 and 7 hours after addition of Alamar Blue. Relative percentage viability at the various concentration of conjugate tested was then calculated versus control (no conjugate) cultures. Cytotoxicities of the conjugates were also compared to the cytotoxicity of unmodified doxorubicin and unmodified oligopeptide assessed in the same assay. Results of this assay are shown in FIG. 7.

What is claimed is:

1. A conjugate which is useful for the treatment of prostate cancer which comprises a cytotoxic agent attached to a oligopeptide, wherein the oligopeptide comprises a sequence of amino acids that is recognized and selectively proteolytically cleaved by free prostate specific antigen and provided that the oligopeptide does not comprise semenogelin I or semenogelin II, wherein the means of attachment is a covalent bond or a chemical linker.

2. The conjugate according to claim 1 wherein the cytotoxic agent is a member of a class of cytotoxic agents selected from the following classes:
   a) anthracycline family of drugs,
   b) the vinca alkaloid drugs,
   c) the mitomycins,
   d) the bleomycins,
   e) the cytotoxic nucleosides,
   f) the pteridine family of drugs,
   g) diynenes,
   h) estramustine,
   i) cyclophosphamide, and
   h) the podophyllotoxins.

3. The conjugate according to claim 1 wherein the cytotoxic agent is selected from the following cytotoxic agents:

a) doxorubicin,
b) carminomycin,
c) daunorubicin,
d) aminopterin,
e) methotrexate,
f) methopterin,
g) dichloro-methotrexate,
h) mitomycin C,
i) porfiromycin,
j) 5-fluorouracil,
k) 6-mercaptopurine,
l) cytosine arabinoside,
m) podophyllotoxin,
n) etoposide,
o) etoposide phosphate,
p) melphalan,
q) vinblastine,
r) vincristine,
s) leurosidine,
t) vindesine,
u) estramustine,
v) cisplatin,
w) cyclophosphamide, and
x) leurosine.

4. The conjugate according to claim 1 wherein the cytotoxic agent is selected from doxorubicin and vinblastine or a cytotoxic derivative thereof.

5. The conjugate according to claim 1 wherein the cytotoxic agent is doxorubicin or a cytotoxic derivative thereof.

6. The conjugate according to claim 5 of the formula I:

I

[Structure of doxorubicin with $X_L$-oligopeptide-R substituent]

wherein:
oligopeptide is an oligopeptide which is specifically recognized by the free prostate specific antigen (PSA) and is capable of being proteolytically cleaved by the enzymatic activity of the free prostate specific antigen;

$X_L$ is absent or is an amino acid selected from:
a) phenylalanine,
b) leucine,
c) valine,
d) isoleucine,
e) (2-naphthyl)alanine,
f) cyclohexylalanine,
g) diphenylalanine,
h) norvaline, and
j) norleucine;

R is hydrogen or —(C=O)$R^1$; and $R^1$ is $C_1$–$C_6$-alkyl or aryl.

7. The conjugate according to claim 6 wherein:
oligopeptide is an oligomer that comprises an amino acid sequence selected from:

a) AsnLysIleSerTyrGln|Ser, (SEQ.ID.NO.: 13)

b) LysIleSerTyrGln|Ser, (SEQ.ID.NO.: 14)

c) GlyGluAsnGlyValGlnLysAspValSerGlnXaa
SerIleTyr|SerGlnThrGlu, (SEQ.ID.NO.: 15)

d) GlyLysGlyIleSerSerGlnTyr|SerAsnThrGluGlu
ArgLeu, (SEQ.ID.NO.: 2)

e) AsnLysIleSerTyrTyr|Ser, (SEQ.ID.NO.: 127)

f) AsnLysAlaSerTyrGln|Ser, (SEQ.ID.NO.: 128)

g) SerTyrGln|SerSer, and (SEQ.ID.NO.: 129)

h) hArgTyrGln|SerSer; (SEQ.ID.NO.: 141)

wherein hArg is homoarginine and Xaa is any natural amino acid;

$X_L$ is absent or is an amino acid selected from:
a) leucine,
b) isoleucine, and
d) valine; and R is acetyl, pivaloyl or benzoyl.

8. The conjugate according to claim 5 which is selected from:

[Structure of doxorubicin with X substituent]

wherein X is:

(SEQ.ID.NO.:13)

$H_2N$—AsnLysIleSerTyrGlnSer-C(=O)—, (SEQ.ID.NO.:16)

$H_2N$—AsnLysIleSerTyrGlnSerSer-C(=O)—, (SEQ.ID.NO.:17)

$H_2N$—AsnLysIleSerTyrGlnSerSerSer-C(=O)—, (SEQ.ID.NO.:10)

$H_2N$—AsnLysIleSerTyrGlnSerSerSerThr-C(=O)—,

H₂N—AsnLysIleSerTyrGlnSerSerThrGlu-C(=O)—, (SEQ.ID.NO.:3)

H₂N—AlaAsnLysIleSerTyrGlnSerSerThrGlu-C(=O)—, (SEQ.ID.NO.:11)

AcHN—AlaAsnLysIleSerTyrGlnSerSerThr-C(=O)—, (SEQ.ID.NO.:117)

AcHN—AlaAsnLysIleSerTyrGlnSerSerThrLeu-C(=O)—, (SEQ.ID.NO.:70)

AcHN—AlaAsnLysAlaSerTyrGlnSerAlaSerThrLeu-C(=O)—, (SEQ.ID.NO.:118)

AcHN—AlaAsnLysAlaSerTyrGlnSerAlaSerLeu-C(=O)—, (SEQ.ID.NO.:119)

AcHN—AlaAsnLysAlaSerTyrGlnSerSerSerLeu-C(=O)—, (SEQ.ID.NO.:120)

AcHN—AlaAsnLysAlaSerTyrGlnSerSerLeu-C(=O)—, (SEQ.ID.NO.:121)

AcHN—SerTyrGlnSerSerSerLeu-C(=O)—, (SEQ.ID.NO.:144)

AcHN—hArgTyrGlnSerSerSerLeu-C(=O)—, (SEQ.ID.NO.:145)

AcHN—LysTyrGlnSerSerSerLeu-C(=O)—, or (SEQ.ID.NO.:124)

AcHN—LysTyrGlnSerSerNle-C(=O)—. (SEQ.ID.NO.:146)

* * * * *

(12) EX PARTE REEXAMINATION CERTIFICATE (5734th)
United States Patent
DeFeo-Jones et al.

(10) Number: US 6,143,864 C1
(45) Certificate Issued: *Apr. 3, 2007

(54) PEPTIDES

(75) Inventors: Deborah DeFeo-Jones, Lansdale, PA (US); Dong-Mei Feng, Harleysville, PA (US); Victor M. Garsky, Blue Bell, PA (US); Raymond E. Jones, Lansdale, PA (US); Allen I. Oliff, Gwynedd Valley, PA (US)

(73) Assignee: Merck & Co., Inc., Rahway, NJ (US)

Reexamination Request:
No. 90/008,027, May 2, 2006

Reexamination Certificate for:
Patent No.: 6,143,864
Issued: Nov. 7, 2000
Appl. No.: 08/468,161
Filed: Jun. 6, 1995

(*) Notice: This patent is subject to a terminal disclaimer.

Related U.S. Application Data

(63) Continuation-in-part of application No. 08/404,833, filed on Mar. 15, 1995, now abandoned, which is a continuation-in-part of application No. 08/267,092, filed on Jun. 28, 1994, now Pat. No. 5,599,686.

(51) Int. Cl.
*A61K 38/00* (2006.01)
*A61K 47/48* (2006.01)
*C07K 14/435* (2006.01)
*C07K 14/47* (2006.01)

(52) U.S. Cl. .................. 530/322; 530/324; 530/326; 530/328; 530/329

(58) Field of Classification Search ............... None
See application file for complete search history.

(56) References Cited

PUBLICATIONS

Isaacs, J. T. et al., "Androgen Regulation of Programmed Cell Death of Normal and Malignant Prostatic Cells", J. Andrology, 13:6 (Nov./Dec. 1992) pp. 457–462.*

Furuya, Y et al., "Proliferation Independent Activation of Programmed Cell Death as a Novel Therapy for Prostate Cancer", Apoptosis (Mihich and Schimke, Eds. Plenum Press, NY, 1994) based on "Proceedings of the Fifth Pezcoller Symp. On Apoptosis, held Jun. 9–11, 1993, in Trento, Italy".*

* cited by examiner

*Primary Examiner*—Bennett Celsa

(57) ABSTRACT

Oligopeptides which comprise amino acid sequences that are recognized and proteolytically cleaved by free prostate specific antigen (PSA) are described. Also described are assays which comprise such oligopeptides useful for determining free PSA protease activity in vitro and in vivo. Therapeutic agents which comprise conjugates of such oligopeptides and known cytotoxic agents are also described.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–8 is confirmed.

* * * * *

SEQUENCE LISTING (1) GENERAL INFORMATION:

(iii) NUMBER OF SEQUENCES: 146

(2) INFORMATION FOR SEQ ID NO:1:

(i) SEQUENCE CHARACTERISTICS:
      (A) LENGTH: 462 amino acids
      (B) TYPE: amino acid
      (C) STRANDEDNESS: single
      (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:1:

```
Met Lys Pro Asn Ile Ile Phe Val Leu Ser Leu Leu Leu Ile Leu Glu
1               5                   10                  15

Lys Gln Ala Ala Val Met Gly Gln Lys Gly Gly Ser Lys Gly Arg Leu
            20                  25                  30

Pro Ser Glu Phe Ser Gln Phe Pro His Gly Gln Lys Gly Gln His Tyr
        35                  40                  45

Ser Gly Gln Lys Gly Lys Gln Gln Thr Glu Ser Lys Gly Ser Phe Ser
    50                  55                  60

Ile Gln Tyr Thr Tyr His Val Asp Ala Asn Asp His Asp Gln Ser Arg
65                  70                  75                  80

Lys Ser Gln Gln Tyr Asp Leu Asn Ala Leu His Lys Thr Thr Lys Ser
                85                  90                  95

Gln Arg His Leu Gly Gly Ser Gln Gln Leu Leu His Asn Lys Gln Glu
            100                 105                 110

Gly Arg Asp His Asp Lys Ser Lys Gly His Phe His Arg Val Val Ile
        115                 120                 125

His His Lys Gly Gly Lys Ala His Arg Gly Thr Gln Asn Pro Ser Gln
    130                 135                 140
```

Asp Gln Gly Asn Ser Pro Ser Gly Lys Gly Ile Ser Ser Gln Tyr Ser
145                 150                 155                 160

Asn Thr Glu Glu Arg Leu Trp Val His Gly Leu Ser Lys Glu Gln Thr
            165                 170                 175

Ser Val Ser Gly Ala Gln Lys Gly Arg Lys Gln Gly Gly Ser Gln Ser
            180                 185                 190

Ser Tyr Val Leu Gln Thr Glu Glu Leu Val Ala Asn Lys Gln Gln Arg
            195                 200                 205

Glu Thr Lys Asn Ser His Gln Asn Lys Gly His Tyr Gln Asn Val Val
    210                 215                 220

Glu Val Arg Glu Glu His Ser Ser Lys Val Gln Thr Ser Leu Cys Pro
225                 230                 235                 240

Ala His Gln Asp Lys Leu Gln His Gly Ser Lys Asp Ile Phe Ser Thr
            245                 250                 255

Gln Asp Glu Leu Leu Val Tyr Asn Lys Asn Gln His Gln Thr Lys Asn
            260                 265                 270

Leu Asn Gln Asp Gln Gln His Gly Arg Lys Ala Asn Lys Ile Ser Tyr
            275                 280                 285

Gln Ser Ser Ser Thr Glu Glu Arg Arg Leu His Tyr Gly Glu Asn Gly
    290                 295                 300

Val Gln Lys Asp Val Ser Gln Ser Ser Ile Tyr Ser Gln Thr Glu Glu
305                 310                 315                 320

Lys Ala Gln Gly Lys Ser Gln Lys Gln Ile Thr Ile Pro Ser Gln Glu
            325                 330                 335

Gln Glu His Ser Gln Lys Ala Asn Lys Ile Ser Tyr Gln Ser Ser Ser
            340                 345                 350

Thr Glu Glu Arg Arg Leu His Tyr Gly Glu Asn Gly Val Gln Lys Asp
            355                 360                 365

Val Ser Gln Arg Ser Ile Tyr Ser Gln Thr Glu Lys Leu Val Ala Gly
    370                 375                 380

Lys Ser Gln Ile Gln Ala Pro Asn Pro Lys Gln Glu Pro Trp His Gly
385                 390                 395                 400

Glu Asn Ala Lys Gly Glu Ser Gly Gln Ser Thr Asn Arg Glu Gln Asp
            405                 410                 415

Leu Leu Ser His Glu Gln Lys Gly Arg His Gln His Gly Ser His Gly
            420                 425                 430

Gly Leu Asp Ile Val Ile Ile Glu Gln Glu Asp Asp Ser Asp Arg His
            435                 440                 445

Leu Ala Gln His Leu Asn Asn Asp Arg Asn Pro Leu Phe Thr
450                 455                 460

(2) INFORMATION FOR SEQ ID NO:2:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:2:

-continued

```
Gly Lys Gly Ile Ser Ser Gln Tyr Ser Asn Thr Glu Glu Arg Leu
1               5                   10                  15
```

(2) INFORMATION FOR SEQ ID NO:3:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:3:

```
Asn Lys Ile Ser Tyr Gln Ser Ser Ser Thr Glu
1               5                   10
```

(2) INFORMATION FOR SEQ ID NO:4:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:4:

```
Gly Glu Asn Gly Val Gln Lys Asp Val Ser Gln Arg Ser Ile Tyr Ser
1               5                   10                  15

Gln Thr Glu
```

(2) INFORMATION FOR SEQ ID NO:5:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:5:

```
Gly Glu Asn Gly Val Gln Lys Asp Val Ser Gln Ser Ser Ile Tyr Ser
1               5                   10                  15

Gln Thr Glu
```

(2) INFORMATION FOR SEQ ID NO:6:

(i) SEQUENCE CHARACTERISTICS:
        (A) LENGTH: 25 amino acids (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:6:

Gly Arg Lys Ala Asn Lys Ile Ser Tyr Gln Ser Ser Ser Thr Glu Glu
1               5                  10                  15

Arg Arg Leu His Tyr Gly Glu Asn Gly
            20                  25

(2) INFORMATION FOR SEQ ID NO:7:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:7:

Ser Tyr Gln Ser Ser Ser Thr Glu
1               5

(2) INFORMATION FOR SEQ ID NO:8:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:8:

Ile Ser Tyr Gln Ser Ser Ser Thr Glu
1               5

(2) INFORMATION FOR SEQ ID NO:9:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:9:

Lys Ile Ser Tyr Gln Ser Ser Ser Thr Glu
1               5                   10

(2) INFORMATION FOR SEQ ID NO:10:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:10:

Asn Lys Ile Ser Tyr Gln Ser Ser Ser Thr
1               5                   10

(2) INFORMATION FOR SEQ ID NO:11:

(i) SEQUENCE CHARACTERISTICS:
            (A) LENGTH: 12 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:11:

Ala Asn Lys Ile Ser Tyr Gln Ser Ser Ser Thr Glu
1               5                   10

(2) INFORMATION FOR SEQ ID NO:12:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:12:

Ala Ser Ala Gly Thr Pro Gly Ala
1               5

(2) INFORMATION FOR SEQ ID NO:13:

(i) SEQUENCE CHARACTERISTICS:
            (A) LENGTH: 7 amino acids
            (B) TYPE: amino acid

```
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:13:

Asn Lys Ile Ser Tyr Gln Ser
1               5

(2) INFORMATION FOR SEQ ID NO:14:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:14:

Lys Ile Ser Tyr Gln Ser
1               5

(2) INFORMATION FOR SEQ ID NO:15:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
        (A) NAME/KEY: Peptide
        (B) LOCATION: 12
        (D) OTHER INFORMATION: /note= "any natural amino acid"

(xi) SEQUENCE DESCRIPTION: SEQ ID NO:15:

Gly Glu Asn Gly Val Gln Lys Asp Val Ser Gln Xaa Ser Ile Tyr Ser
1               5                   10                  15

Gln Thr Glu (2) INFORMATION FOR SEQ ID NO:16:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO
```

```
       (iv) ANTI-SENSE: NO (v) FRAGMENT TYPE: internal (xi) SEQUENCE DESCRIPTION: SEQ ID NO:16:

Asn Lys Ile Ser Tyr Gln Ser Ser
1               5

(2) INFORMATION FOR SEQ ID NO:17:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:17:

Asn Lys Ile Ser Tyr Gln Ser Ser Ser
1               5

(2) INFORMATION FOR SEQ ID NO:18:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:18:

Ala Asn Lys Ile Ser Tyr Gln Ser Ser Ser
1               5                   10

(2) INFORMATION FOR SEQ ID NO:19:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:19:

Lys Ile Ser Tyr Gln Ser Ser Ser Thr Glu
1               5                   10

(2) INFORMATION FOR SEQ ID NO:20:
```

```
        (i) SEQUENCE CHARACTERISTICS:
            (A) LENGTH: 17 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:20:

Gln Leu Asp Asn Lys Ile Ser Tyr Gln Ser Ser Ser Thr His Gln Ser
1               5                  10                  15

Ser (2) INFORMATION FOR SEQ ID NO:21:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:21:

Asn Arg Ile Ser Tyr Gln Ser
1               5

(2) INFORMATION FOR SEQ ID NO:22:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:22:

Asn Lys Val Ser Tyr Gln Ser
1               5

(2) INFORMATION FOR SEQ ID NO:23:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: protein (iii) HYPOTHETICAL: NO (iv) ANTI-SENSE: NO
```

```
        (v) FRAGMENT TYPE: internal (xi) SEQUENCE DESCRIPTION: SEQ ID NO:23:

Asn Lys Met Ser Tyr Gln Ser Ser
1               5

(2) INFORMATION FOR SEQ ID NO:24:

(i) SEQUENCE CHARACTERISTICS:
           (A) LENGTH: 8 amino acids
           (B) TYPE: amino acid
           (C) STRANDEDNESS: single
           (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:24:

Asn Lys Leu Ser Tyr Gln Ser Ser
1               5

(2) INFORMATION FOR SEQ ID NO:25:

(i) SEQUENCE CHARACTERISTICS:
           (A) LENGTH: 9 amino acids
           (B) TYPE: amino acid
           (C) STRANDEDNESS: single
           (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:25:

Asn Lys Ile Thr Tyr Gln Ser Ser Ser
1               5

(2) INFORMATION FOR SEQ ID NO:26:

(i) SEQUENCE CHARACTERISTICS:
           (A) LENGTH: 9 amino acids
           (B) TYPE: amino acid
           (C) STRANDEDNESS: single
           (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:26:

Asn Lys Ile Ser Phe Gln Ser Ser Ser
1               5

(2) INFORMATION FOR SEQ ID NO:27:

(i) SEQUENCE CHARACTERISTICS:
           (A) LENGTH: 10 amino acids
```

(B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:27:

Asn Lys Ile Ser Trp Gln Ser Ser Ser Thr
1               5                   10

(2) INFORMATION FOR SEQ ID NO:28:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:28:

Asn Lys Ile Ser Tyr Asn Ser Ser Ser Thr
1               5                   10

(2) INFORMATION FOR SEQ ID NO:29:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:29:

Asn Lys Ile Ser Tyr Gln Thr Ser Ser Thr
1               5                   10

(2) INFORMATION FOR SEQ ID NO:30:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:30:

```
Asn Lys Ile Ser Tyr Gln Ser
1               5
```

(2) INFORMATION FOR SEQ ID NO:31:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:31:

```
Gln Lys Ile Ser Tyr Gln Ser Ser
1               5
```

(2) INFORMATION FOR SEQ ID NO:32:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:32:

```
Asn Arg Ile Thr Tyr Gln Ser Ser Ser
1               5
```

(2) INFORMATION FOR SEQ ID NO:33:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:33:

```
Asn Arg Ile Ser Phe Gln Ser Ser Ser Thr
1               5                   10
```

(2) INFORMATION FOR SEQ ID NO:34:

(i) SEQUENCE CHARACTERISTICS:
        (A) LENGTH: 10 amino acids
        (B) TYPE: amino acid
        (C) STRANDEDNESS: single
        (D) TOPOLOGY: linear

```
        (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:34:

Gln Lys Ile Ser Tyr Gln Thr Ser Ser Thr
1               5                  10

(2) INFORMATION FOR SEQ ID NO:35:

(i) SEQUENCE CHARACTERISTICS:
             (A) LENGTH: 10 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:35:

Asn Arg Ile Ser Trp Gln Ser Ser Ser Thr
1               5                  10

(2) INFORMATION FOR SEQ ID NO:36:

(i) SEQUENCE CHARACTERISTICS:
             (A) LENGTH: 10 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:36:

Asn Arg Ile Ser Tyr Gln Thr Ser Ser Thr
1               5                  10

(2) INFORMATION FOR SEQ ID NO:37:

(i) SEQUENCE CHARACTERISTICS:
             (A) LENGTH: 10 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:37:

Asn Lys Ile Thr Tyr Gln Thr Ser Ser Thr
1               5                  10
```

```
(2) INFORMATION FOR SEQ ID NO:38:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:38:

Asn Lys Leu Ser Tyr Gln Thr Ser Ser Thr
1               5                   10

(2) INFORMATION FOR SEQ ID NO:39:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:39:

Gln Lys Leu Ser Tyr Gln Ser Ser Ser Thr
1               5                   10

(2) INFORMATION FOR SEQ ID NO:40:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:40:

Asn Arg Leu Ser Tyr Gln Thr Ser Ser Thr
1               5                   10

(2) INFORMATION FOR SEQ ID NO:41:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (iii) HYPOTHETICAL: NO
```

(iv) ANTI-SENSE: NO (v) FRAGMENT TYPE: internal (xi) SEQUENCE DESCRIPTION: SEQ ID NO:41:

Asn Lys Val Ser Phe Gln Ser Ser Ser Thr
1               5                   10

(2) INFORMATION FOR SEQ ID NO:42:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:42:

Asn Arg Val Ser Trp Gln Ser Ser Ser Thr
1               5                   10

(2) INFORMATION FOR SEQ ID NO:43:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:43:

Gln Lys Val Ser Tyr Gln Ser Ser Ser Thr
1               5                   10

(2) INFORMATION FOR SEQ ID NO:44:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:44:

Asn Lys Ile Ser Tyr Gln Ser Ser Ser Thr
1               5                   10

(2) INFORMATION FOR SEQ ID NO:45:

(i) SEQUENCE CHARACTERISTICS:

(A) LENGTH: 19 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:45:

Gly Glu Gln Gly Val Gln Lys Asp Val Ser Gln Ser Ser Ile Tyr Ser
1               5                   10                  15

Gln Thr Glu (2) INFORMATION FOR SEQ ID NO:46:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:46:

Gly Lys Gly Ile Ser Ser Gln Tyr Ser Asn Thr Asp Glu Arg Leu
1               5                   10                  15

(2) INFORMATION FOR SEQ ID NO:47:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:47:

Gly Glu Asn Gly Leu Gln Lys Asp Val Ser Gln Ser Ser Ile Tyr Ser
1               5                   10                  15

Gln Thr Glu (2) INFORMATION FOR SEQ ID NO:48:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:48:

Gly Glu Asn Gly Val Asn Lys Asp Val Ser Gln Ser Ser Ile Tyr Ser
1               5                  10                  15

Gln Thr Glu (2) INFORMATION FOR SEQ ID NO:49:

(i) SEQUENCE CHARACTERISTICS:
         (A) LENGTH: 19 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:49:

Gly Glu Asn Gly Val Gln Arg Asp Val Ser Gln Arg Ser Ile Tyr Ser
1               5                  10                  15

Gln Thr Glu (2) INFORMATION FOR SEQ ID NO:50:

(i) SEQUENCE CHARACTERISTICS:
         (A) LENGTH: 19 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:50:

Gly Glu Asn Gly Val Gln Lys Asp Val Ser Gln Lys Ser Ile Tyr Ser
1               5                  10                  15

Gln Thr Glu (2) INFORMATION FOR SEQ ID NO:51:

(i) SEQUENCE CHARACTERISTICS:
         (A) LENGTH: 19 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:51:

Gly Glu Asn Gly Val Gln Lys Asp Leu Ser Gln Thr Ser Ile Tyr Ser

```
                 1               5              10              15
Gln Thr Glu (2) INFORMATION FOR SEQ ID NO:52:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:52:

Gly Glu Asn Gly Val Gln Lys Asp Val Ser Gln Ser Ser Ile Phe Ser
 1               5                  10                  15
Gln Thr Glu (2) INFORMATION FOR SEQ ID NO:53:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:53:

Gly Glu Asn Gly Val Gln Lys Asp Met Ser Gln Ser Ser Ile Tyr Thr
 1               5                  10                  15
Gln Thr Glu (2) INFORMATION FOR SEQ ID NO:54:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:54:

Gly Glu Asn Gly Val Gln Lys Asp Val Ser Gln Arg Ser Ile Tyr Thr
 1               5                  10                  15
Gln Thr Glu (2) INFORMATION FOR SEQ ID NO:55:
```

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:55:

Gly Glu Asn Gly Val Gln Lys Asp Val Ser Gln Ser Ser Ile Tyr Ser
1               5                  10                  15

Gln Ser Glu (2) INFORMATION FOR SEQ ID NO:56:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:56:

Gly Glu Asn Gly Val Gln Lys Asp Val Ser Gln Arg Ser Ile Tyr Ser
1               5                  10                  15

Asn Thr Glu (2) INFORMATION FOR SEQ ID NO:57:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:57:

Gly Lys Ala Ile Ser Ser Gln Tyr Ser Asn Thr Glu Glu Arg Leu
1               5                  10                  15

(2) INFORMATION FOR SEQ ID NO:58:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:58:

Gly Lys Gly Ile Ser Ser Gln Tyr Ser Asn Ser Glu Glu Arg Leu
1               5                   10                  15

(2) INFORMATION FOR SEQ ID NO:59:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:59:

Gly Arg Gly Ile Ser Ser Gln Tyr Ser Asn Thr Glu Glu Arg Leu
1               5                   10                  15

(2) INFORMATION FOR SEQ ID NO:60:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:60:

Gly Lys Gly Ile Thr Ser Gln Tyr Ser Asn Thr Glu Glu Arg Leu
1               5                   10                  15

(2) INFORMATION FOR SEQ ID NO:61:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:61:

Gly Lys Gly Ile Ser Thr Gln Tyr Ser Asn Thr Glu Glu Arg Leu
1               5                   10                  15

(2) INFORMATION FOR SEQ ID NO:62:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:62:

Gly Lys Gly Ile Ser Ser Asn Tyr Ser Asn Thr Glu Glu Arg Leu
1               5                   10                  15

(2) INFORMATION FOR SEQ ID NO:63:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:63:

Ala Lys Gly Ile Ser Ser Gln Tyr Ser Asn Thr Glu Glu Arg Leu
1               5                   10                  15

(2) INFORMATION FOR SEQ ID NO:64:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:64:

Gly Lys Gly Ile Ser Ser Gln Phe Ser Asn Thr Glu Glu Arg Leu
1               5                   10                  15

(2) INFORMATION FOR SEQ ID NO:65:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal

```
    (xi) SEQUENCE DESCRIPTION: SEQ ID NO:65:

Gly Lys Gly Ile Ser Ser Gln Tyr Thr Asn Ser Glu Glu Arg Leu
1               5                   10                  15

(2) INFORMATION FOR SEQ ID NO:66:

(i) SEQUENCE CHARACTERISTICS:
         (A) LENGTH: 15 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:66:

Gly Lys Gly Ile Ser Ser Gln Tyr Ser Asn Ser Glu Glu Arg Leu
1               5                   10                  15

(2) INFORMATION FOR SEQ ID NO:67:

(i) SEQUENCE CHARACTERISTICS:
         (A) LENGTH: 25 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:67:

Ser Gln Lys Ala Asn Lys Ile Ser Tyr Gln Ser Ser Ser Thr Glu Glu
1               5                   10                  15

Arg Arg Leu His Tyr Gly Glu Asn Gly
            20                  25

(2) INFORMATION FOR SEQ ID NO:68:

(i) SEQUENCE CHARACTERISTICS:
         (A) LENGTH: 8 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:68:

Ile Ser Tyr Gln Ser Ser Ser Thr
1               5

(2) INFORMATION FOR SEQ ID NO:69:

(i) SEQUENCE CHARACTERISTICS:
```

(A) LENGTH: 9 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:69:

Ala Asn Lys Ile Ser Tyr Gln Ser Ser
1               5

(2) INFORMATION FOR SEQ ID NO:70:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:70:

Ala Asn Lys Ile Ser Tyr Gln Ser Ser Ser Thr Leu
1               5                   10

(2) INFORMATION FOR SEQ ID NO:71:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:71:

Ala Asn Gly Ile Ser Tyr Gln Ser Ser Ser Thr Glu
1               5                   10

(2) INFORMATION FOR SEQ ID NO:72:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal

```
        (xi) SEQUENCE DESCRIPTION: SEQ ID NO:72:

Ala Asn Pro Ile Ser Tyr Gln Ser Ser Ser Thr Glu
1               5                   10

(2) INFORMATION FOR SEQ ID NO:73:

(i) SEQUENCE CHARACTERISTICS:
          (A) LENGTH: 12 amino acids
          (B) TYPE: amino acid
          (C) STRANDEDNESS: single
          (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:73:

Ala Asn Lys Ile Ser Tyr Gln Ser Ala Ser Thr Glu
1               5                   10

(2) INFORMATION FOR SEQ ID NO:74:

(i) SEQUENCE CHARACTERISTICS:
          (A) LENGTH: 12 amino acids
          (B) TYPE: amino acid
          (C) STRANDEDNESS: single
          (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:74:

Ala Asn Lys Ile Ser Tyr Gln Ser Ser Lys Thr Glu
1               5                   10

(2) INFORMATION FOR SEQ ID NO:75:

(i) SEQUENCE CHARACTERISTICS:
          (A) LENGTH: 11 amino acids
          (B) TYPE: amino acid
          (C) STRANDEDNESS: single
          (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:75:

Ala Asn Lys Ile Ser Tyr Gln Ser Ser Thr Glu
1               5                   10

(2) INFORMATION FOR SEQ ID NO:76:

(i) SEQUENCE CHARACTERISTICS:
          (A) LENGTH: 12 amino acids
          (B) TYPE: amino acid
          (C) STRANDEDNESS: single
          (D) TOPOLOGY: linear
```

(ii) MOLECULE TYPE: peptide (iii) HYPOTHETICAL: NO (iv) ANTI-SENSE: NO (v) FRAGMENT TYPE: internal (ix) FEATURE:
         (A) NAME/KEY: Peptide
         (B) LOCATION: 5
         (D) OTHER INFORMATION: /label= d-serine
              /note= "unnatural configuration of the amino acid"

(xi) SEQUENCE DESCRIPTION: SEQ ID NO:76:

Ala Asn Lys Ile Ser Tyr Gln Ser Ser Ser Thr Glu
1               5                  10

(2) INFORMATION FOR SEQ ID NO:77:

(i) SEQUENCE CHARACTERISTICS:
         (A) LENGTH: 12 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
         (A) NAME/KEY: Peptide
         (B) LOCATION: 4
         (D) OTHER INFORMATION: /label= d-isoleucine
              /note= "unnatural amino acid stereochemical configuration"

(xi) SEQUENCE DESCRIPTION: SEQ ID NO:77:

Ala Asn Lys Ile Ser Tyr Gln Ser Ser Ser Thr Glu
1               5                  10

(2) INFORMATION FOR SEQ ID NO:78:

(i) SEQUENCE CHARACTERISTICS:
         (A) LENGTH: 12 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:78:

Ala Asn Lys Ile Ser Tyr Gln Ser Ser Gln Thr Glu
1               5                  10

(2) INFORMATION FOR SEQ ID NO:79:

(i) SEQUENCE CHARACTERISTICS:
         (A) LENGTH: 12 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:79:

Ala Asn Lys Ile Ser Tyr Gln Ser Ala Lys Thr Glu
1               5                  10

(2) INFORMATION FOR SEQ ID NO:80:

(i) SEQUENCE CHARACTERISTICS:
             (A) LENGTH: 12 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
             (A) NAME/KEY: Peptide
             (B) LOCATION: 3
             (D) OTHER INFORMATION: /label= d-lysine
                  /note= "unnatural amino acid stereochemical
                  configuration"

(xi) SEQUENCE DESCRIPTION: SEQ ID NO:80:

Ala Asn Lys Ile Ser Tyr Gln Ser Ser Ser Thr Glu
1               5                  10

(2) INFORMATION FOR SEQ ID NO:81:

(i) SEQUENCE CHARACTERISTICS:
             (A) LENGTH: 10 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:81:

Ala Asn Lys Ile Ser Tyr Gln Ser Thr Glu
1               5                  10

(2) INFORMATION FOR SEQ ID NO:82:

(i) SEQUENCE CHARACTERISTICS:
             (A) LENGTH: 10 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:82:

Ala Asn Lys Ser Tyr Gln Ser Ser Thr Glu
1               5                   10

(2) INFORMATION FOR SEQ ID NO:83:

(i) SEQUENCE CHARACTERISTICS:
         (A) LENGTH: 10 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:83:

Ala Asn Lys Ile Tyr Gln Ser Ser Thr Glu
1               5                   10

(2) INFORMATION FOR SEQ ID NO:84:

(i) SEQUENCE CHARACTERISTICS:
         (A) LENGTH: 12 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:84:

Ala Asn Lys Ala Ser Tyr Gln Ser Ala Ser Thr Glu
1               5                   10

(2) INFORMATION FOR SEQ ID NO:85:

(i) SEQUENCE CHARACTERISTICS:
         (A) LENGTH: 12 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:85:

Ala Asn Glu Ile Ser Tyr Gln Ser Ala Ser Thr Glu
1               5                   10

(2) INFORMATION FOR SEQ ID NO:86:

(i) SEQUENCE CHARACTERISTICS:
         (A) LENGTH: 7 amino acids
         (B) TYPE: amino acid

```
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:86:

Lys Ile Ser Tyr Gln Ser Ser
1               5

(2) INFORMATION FOR SEQ ID NO:87:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:87:

Ser Tyr Gln Ser Ser Thr Glu
1               5

(2) INFORMATION FOR SEQ ID NO:88:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:88:

Ser Tyr Gln Ser Ser Thr Leu
1               5

(2) INFORMATION FOR SEQ ID NO:89:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:89:
```

```
Ala Ser Tyr Gln Ser Ser Thr Glu
1               5
```

(2) INFORMATION FOR SEQ ID NO:90:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:90:

```
Glu Ile Ser Tyr Gln Ser Ser Ser Thr Glu
1               5                   10
```

(2) INFORMATION FOR SEQ ID NO:91:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:91:

```
Ala Asn Glu Ile Ser Tyr Gln Ser Ser Ser Thr Glu
1               5                   10
```

(2) INFORMATION FOR SEQ ID NO:92:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:92:

```
Ala Asn Lys Ile Ser Tyr Tyr Ser Ser Ser Thr Glu
1               5                   10
```

(2) INFORMATION FOR SEQ ID NO:93:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:93:

Ala Asn Lys Ile Ser Tyr Tyr Ser Ala Ser Thr Glu
1               5                  10

(2) INFORMATION FOR SEQ ID NO:94:

(i) SEQUENCE CHARACTERISTICS:
             (A) LENGTH: 7 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:94:

Ala Ser Tyr Gln Ser Ser Leu
1               5

(2) INFORMATION FOR SEQ ID NO:95:

(i) SEQUENCE CHARACTERISTICS:
             (A) LENGTH: 10 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:95:

Ala Asn Ser Tyr Gln Ser Ser Ser Thr Glu
1               5                  10

(2) INFORMATION FOR SEQ ID NO:96:

(i) SEQUENCE CHARACTERISTICS:
             (A) LENGTH: 9 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:96:

Ala Ser Tyr Gln Ser Ser Ser Thr Glu
1               5

(2) INFORMATION FOR SEQ ID NO:97:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:97:

```
Ser Tyr Gln Ser Ser Ser Thr Glu
1               5
```

(2) INFORMATION FOR SEQ ID NO:98:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:98:

```
Ala Asn Lys Ala Ser Tyr Gln Ser Ala Ser Cys
1               5                   10
```

(2) INFORMATION FOR SEQ ID NO:99:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:99:

```
Gln Ser Ser Thr Glu
1               5
```

(2) INFORMATION FOR SEQ ID NO:100:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO

```
        (v) FRAGMENT TYPE: internal (xi) SEQUENCE DESCRIPTION: SEQ ID NO:100:

Tyr Gln Ser Ser Thr Glu
1               5

(2) INFORMATION FOR SEQ ID NO:101:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:101:

Ser Gln Ser Ser Thr Glu
1               5

(2) INFORMATION FOR SEQ ID NO:102:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:102:

Ala Asn Lys Ile Ser Gln Ser Ser Thr Glu
1               5                   10

(2) INFORMATION FOR SEQ ID NO:103:

(i) SEQUENCE CHARACTERISTICS:
            (A) LENGTH: 11 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
            (A) NAME/KEY: Peptide
            (B) LOCATION: 3
            (D) OTHER INFORMATION: /label= unnatural
                /note= "ornithine"

(xi) SEQUENCE DESCRIPTION: SEQ ID NO:103:

Ala Asn Xaa Ile Ser Tyr Gln Ser Ser Thr Glu
1               5                   10
```

(2) INFORMATION FOR SEQ ID NO:104:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
        (A) NAME/KEY: Peptide
        (B) LOCATION: 2
        (D) OTHER INFORMATION: /label= unnatural
            /note= "3,4-dichlorophenalanine"

(xi) SEQUENCE DESCRIPTION: SEQ ID NO:104:

Ser Xaa Gln Ser Ser Thr Glu
1               5

(2) INFORMATION FOR SEQ ID NO:105:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
        (A) NAME/KEY: Peptide
        (B) LOCATION: 2
        (D) OTHER INFORMATION: /label= unnatural
            /note= "(3-pyridinyl)alanine"

(xi) SEQUENCE DESCRIPTION: SEQ ID NO:105:

Ser Xaa Gln Ser Ser Thr Glu
1               5

(2) INFORMATION FOR SEQ ID NO:106:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:106:

Ser Lys Gln Ser Ser Thr Glu
1               5

(2) INFORMATION FOR SEQ ID NO:107:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:107:

```
Ser Tyr Gln Ser Ser Ser Leu
1               5
```

(2) INFORMATION FOR SEQ ID NO:108:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: internal (ix) FEATURE:
        (A) NAME/KEY: Peptide
        (B) LOCATION: 1
        (D) OTHER INFORMATION: /label= unnatural
            /note= "epsilon aminocaproic acid"

(xi) SEQUENCE DESCRIPTION: SEQ ID NO:108:

```
Xaa Tyr Gln Ser Ser Ser Leu
1               5
```

(2) INFORMATION FOR SEQ ID NO:109:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
        (A) NAME/KEY: Peptide
        (B) LOCATION: 4
        (D) OTHER INFORMATION: /label= unnatural
            /note= "N-methylisoleucine"

(xi) SEQUENCE DESCRIPTION: SEQ ID NO:109:

```
Ala Asn Lys Xaa Ser Tyr Gln Ser Ser Thr Glu
1               5                   10
```

```
(2) INFORMATION FOR SEQ ID NO:110:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:110:

Ser Tyr Gln Ser Ser Thr Glu
1               5

(2) INFORMATION FOR SEQ ID NO:111:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:111:

Tyr Gln Ser Ser Thr Glu
1               5

(2) INFORMATION FOR SEQ ID NO:112:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:112:

Ser Tyr Lys Ser Ser Thr Glu
1               5

(2) INFORMATION FOR SEQ ID NO:113:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO
```

```
        (v) FRAGMENT TYPE: internal (xi) SEQUENCE DESCRIPTION: SEQ ID NO:113:

Ser Tyr Tyr Ser Ser Thr Glu
1               5

(2) INFORMATION FOR SEQ ID NO:114:

(i) SEQUENCE CHARACTERISTICS:
          (A) LENGTH: 6 amino acids
          (B) TYPE: amino acid
          (C) STRANDEDNESS: single
          (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:114:

Ser Tyr Gln Ser Ser Leu
1               5

(2) INFORMATION FOR SEQ ID NO:115:

(i) SEQUENCE CHARACTERISTICS:
          (A) LENGTH: 6 amino acids
          (B) TYPE: amino acid
          (C) STRANDEDNESS: single
          (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:115:

Ser Tyr Gln Ser Ser Leu
1               5

(2) INFORMATION FOR SEQ ID NO:116:

(i) SEQUENCE CHARACTERISTICS:
          (A) LENGTH: 7 amino acids
          (B) TYPE: amino acid
          (C) STRANDEDNESS: single
          (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
          (A) NAME/KEY: Peptide
          (B) LOCATION: 1
          (D) OTHER INFORMATION: /label= unnatural
              /note= "2,3-diaminopropionic acid"

(xi) SEQUENCE DESCRIPTION: SEQ ID NO:116:

Xaa Tyr Gln Ser Ser Ser Leu
1               5
```

(2) INFORMATION FOR SEQ ID NO:117:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:117:

Ala Asn Lys Ile Ser Tyr Gln Ser Ser Ser Thr
1               5                   10

(2) INFORMATION FOR SEQ ID NO:118:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:118:

Ala Asn Lys Ala Ser Tyr Gln Ser Ala Ser Thr Leu
1               5                   10

(2) INFORMATION FOR SEQ ID NO:119:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:119:

Ala Asn Lys Ala Ser Tyr Gln Ser Ala Ser Leu
1               5                   10

(2) INFORMATION FOR SEQ ID NO:120:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:120:

Ala Asn Lys Ala Ser Tyr Gln Ser Ser Ser Leu
1               5                   10

(2) INFORMATION FOR SEQ ID NO:121:

(i) SEQUENCE CHARACTERISTICS:
             (A) LENGTH: 10 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:121:

Ala Asn Lys Ala Ser Tyr Gln Ser Ser Leu
1               5                   10

(2) INFORMATION FOR SEQ ID NO:122:

(i) SEQUENCE CHARACTERISTICS:
             (A) LENGTH: 7 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
             (A) NAME/KEY: Peptide
             (B) LOCATION: 7
             (D) OTHER INFORMATION: /label= d-leucine
                 /note= "unnatural amino acid stereochemical
                 configuration"

(xi) SEQUENCE DESCRIPTION: SEQ ID NO:122:

Ser Tyr Gln Ser Ser Thr Leu
1               5

(2) INFORMATION FOR SEQ ID NO:123:

(i) SEQUENCE CHARACTERISTICS:
             (A) LENGTH: 11 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:123:

```
Ala Asn Lys Ala Ser Tyr Ala Ser Ser Ser Leu
1               5                   10
```

(2) INFORMATION FOR SEQ ID NO:124:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:124:

```
Lys Tyr Gln Ser Ser Ser Leu
1               5
```

(2) INFORMATION FOR SEQ ID NO:125:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:125:

```
Ser Tyr Gln Ser Ser Lys Leu
1               5
```

(2) INFORMATION FOR SEQ ID NO:126:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
        (A) NAME/KEY: Peptide
        (B) LOCATION: 7
        (D) OTHER INFORMATION: /label= d-leucine
            /note= "unnatural amino acid stereochemical
            configuration"

(xi) SEQUENCE DESCRIPTION: SEQ ID NO:126:

```
Ser Tyr Gln Ser Ser Lys Leu
1               5
```

(2) INFORMATION FOR SEQ ID NO:127:

```
        (i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:127:

Asn Lys Ile Ser Tyr Tyr Ser
1               5

(2) INFORMATION FOR SEQ ID NO:128:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:128:

Asn Lys Ala Ser Tyr Gln Ser
1               5

(2) INFORMATION FOR SEQ ID NO:129:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:129:

Ser Tyr Gln Ser Ser
1               5

(2) INFORMATION FOR SEQ ID NO:130:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO
```

(v) FRAGMENT TYPE: internal (xi) SEQUENCE DESCRIPTION: SEQ ID NO:130:

Asn Lys Ile Ser Tyr Gln Ser Ala
1               5

(2) INFORMATION FOR SEQ ID NO:131:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:131:

Ala Asn Lys Ile Ser Tyr Tyr Ser
1               5

(2) INFORMATION FOR SEQ ID NO:132:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:132:

Ala Asn Lys Ala Ser Tyr Gln Ser
1               5

(2) INFORMATION FOR SEQ ID NO:133:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:133:

Ser Tyr Gln Ser Ser Thr
1               5

(2) INFORMATION FOR SEQ ID NO:134:

(i) SEQUENCE CHARACTERISTICS:
        (A) LENGTH: 6 amino acids
        (B) TYPE: amino acid

```
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:134:

Ser Tyr Gln Ser Ser Ser
1               5

(2) INFORMATION FOR SEQ ID NO:135:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:135:

Ser Tyr Gln Ser Ser Leu
1               5

(2) INFORMATION FOR SEQ ID NO:136:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:136:

Ala Asn Lys Ile Ser Tyr Gln Ser Ala
1               5

(2) INFORMATION FOR SEQ ID NO:137:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:137:
```

```
Ala Asn Lys Ile Ser Tyr Tyr Ser Ser
1               5
```

(2) INFORMATION FOR SEQ ID NO:138:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:138:

```
Ala Asn Lys Ile Ser Tyr Tyr Ser Ala
1               5
```

(2) INFORMATION FOR SEQ ID NO:139:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:139:

```
Ala Asn Lys Ala Ser Tyr Gln Ser Ala
1               5
```

(2) INFORMATION FOR SEQ ID NO:140:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:140:

```
Lys Tyr Gln Ser Ser
1               5
```

(2) INFORMATION FOR SEQ ID NO:141:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
    (A) NAME/KEY: Peptide
    (B) LOCATION: 1
    (D) OTHER INFORMATION: /label= homoarginine (xi) SEQUENCE DESCRIPTION: SEQ ID NO:141:

```
Xaa Tyr Gln Ser Ser
1               5
```

(2) INFORMATION FOR SEQ ID NO:142:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:142:

```
Lys Tyr Gln Ser Ser Ser
1               5
```

(2) INFORMATION FOR SEQ ID NO:143:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
        (A) NAME/KEY: Peptide
        (B) LOCATION: 1
        (D) OTHER INFORMATION: /label= homoarginine (xi) SEQUENCE DESCRIPTION: SEQ ID NO:143:

```
Xaa Tyr Gln Ser Ser Ser
1               5
```

(2) INFORMATION FOR SEQ ID NO:144:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (iii) HYPOTHETICAL: NO

```
        (iv) ANTI-SENSE: NO (v) FRAGMENT TYPE: internal (xi) SEQUENCE DESCRIPTION: SEQ ID NO:144:

Ser Tyr Gln Ser Ser Ser Leu
1               5

(2) INFORMATION FOR SEQ ID NO:145:

(i) SEQUENCE CHARACTERISTICS:
             (A) LENGTH: 7 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
             (A) NAME/KEY: Peptide
             (B) LOCATION: 1
             (D) OTHER INFORMATION: /label= homoarginine (xi) SEQUENCE DESCRIPTION: SEQ ID NO:145:

Xaa Tyr Gln Ser Ser Ser Leu
1               5

(2) INFORMATION FOR SEQ ID NO:146:

(i) SEQUENCE CHARACTERISTICS:
             (A) LENGTH: 7 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
             (A) NAME/KEY: Peptide
             (B) LOCATION: 7
             (D) OTHER INFORMATION: /label= norleucine (xi) SEQUENCE DESCRIPTION: SEQ ID NO:146:

Lys Tyr Gln Ser Ser Ser Leu
1               5
```